United States Patent
Chen et al.

(10) Patent No.: US 10,611,739 B2
(45) Date of Patent: Apr. 7, 2020

(54) PROCESS FOR PREPARATION OF LACTONE DERIVATIVES AND INTERMEDIATES THEREOF

(71) Applicant: PHARMARESOURCES (SHANGHAI) CO., LTD., Shanghai (CN)

(72) Inventors: Ping Chen, Shanghai (CN); Shaoping Peng, Shanghai (CN); Yinqiang Li, Shanghai (CN); Dafeng Li, Shanghai (CN); Xuejun Dong, Shanghai (CN)

(73) Assignee: PHARMARESOURCES (SHANGHAI) CO., LTD. (CN)

( * ) Notice: Subject to any disclaimer, the term of this patent is extended or adjusted under 35 U.S.C. 154(b) by 0 days.

(21) Appl. No.: 16/326,239

(22) PCT Filed: Aug. 16, 2016

(86) PCT No.: PCT/CN2016/095527
§ 371 (c)(1),
(2) Date: Feb. 18, 2019

(87) PCT Pub. No.: WO2018/032356
PCT Pub. Date: Feb. 22, 2018

(65) Prior Publication Data
US 2019/0210981 A1 Jul. 11, 2019

(51) Int. Cl.
*C07D 263/26* (2006.01)
*C07D 307/33* (2006.01)

(52) U.S. Cl.
CPC ......... *C07D 263/26* (2013.01); *C07D 307/33* (2013.01); *Y02P 20/55* (2015.11)

(58) Field of Classification Search
CPC .................................................. C07D 263/26
See application file for complete search history.

(56) References Cited

FOREIGN PATENT DOCUMENTS

| WO | 2008090046 | 7/2008 |
| WO | 2014108525 | 7/2014 |

OTHER PUBLICATIONS

Patent Cooperation Treaty (PCT), International Search Report and Written Opinion for Application PCT/CN/2016/095527 filed Aug. 16, 2016, dated May 15, 2017, International Searching Authority, CN.

*Primary Examiner* — Golam M Shameem
(74) *Attorney, Agent, or Firm* — McDonald Hopkins LLC

(57) ABSTRACT

A novel process for the preparation of lactone derivatives, and intermediates thereof is described. The lactone derivatives are important precursors for the synthesis of anti-hepatitis C virus agents, including sofosbuvir.

3 Claims, No Drawings

PROCESS FOR PREPARATION OF LACTONE DERIVATIVES AND INTERMEDIATES THEREOF

CROSS-REFERENCE TO RELATED APPLICATION

This application is a 35 U.S.C. 371 national stage filing of PCT Application No. PCT/CN2016/095527 filed on Aug. 16, 2016 which is incorporated herein in its entirety by reference.

FIELD OF THE INVENTION

The present invention relates to a novel process for the preparation of lactone derivatives, and to novel intermediates thereof. In particular, this invention relates to a more efficient process for the preparation of lactone derivatives, which are important precursors for the synthesis of anti-hepatitis C virus agents, including sofosbuvir.

BACKGROUND OF THE INVENTION

Hepatitis C virus (HCV) infection represents a global health thereat in need of more effective treatment options. The World Health Organization (WHO) estimates that 130-170 million of individuals worldwide have detectable antibodies to HCV and approximately 60-85% of this population develops into chronic disease, leading to liver cirrhosis (5-25%) and hepatocellular carcinoma (1-3%) and liver failure. While there were existing therapeutics including pegylated interferon-□ (Peg-IFN) and ribavirin (RBV), they are suboptimal due to various adverse effects, intolerability, low efficacy and slow response in reducing the viral loads across the multiple genotypes (1-6) of HCV. Therefore, there is an urgent and enormous need to develop more effective and efficacious novel anti-HCV therapies.

During the past decade, there have been a variety of small molecule agents as direct-acting antivirals (DAAs) targeting HCV viral replication via action on both structural and nonstructural proteins (NS3-5) have been launched in market or in late-stage clinical development. Among the DAAs reported, Soforsbuvir (brand name Sovaldi) targeting NS5B protein from Gilead was approved by FDA in 2003 for HCV genotypes 2 and 3 (in combination with Ribavin). In 2014, a combination of Sofosbuvir with viral NS5A inhibitor Ledipasvir (brand name Harvoni) was approved. This combination provides high cure rates in people infected with HCV genotype 1, the most common subtype in the US, Japan, and much of the Europe, without the use of interferon, and irrespective of prior treatment failure or the presence of cirrhosis. Compared to previous treatment, Sofosbuvir-based regimens provide a higher cure rate, fewer side effects, and a 2-4 fold reduced duration of therapy.

Sofosbuvir is a prodrug using the ProTide biotechnology strategy. It is metabolized to the active antiviral agent 2'-deoxy-2'-α-fluoro-β-C-methyluridine-5'-triphosphate. The triphosphate serves as a defective substrate for the NS5B protein, which is the viral RNA polymerase, thus acts as an inhibitor of viral RNA synthesis.

Due to the tremendous success in Sorosbuvir-based oral therapy, there remains a need for a more efficient method for making sofosbuvir-like anti-hepatitis C virus agents, including sofosbuvir and intermediates thereof. A variety of methods describing different synthetic approaches for substituted lactone (VI) shown below, a key intermediate for Sofosbuvir and its like anti-viral drugs have been published.

WO2008045419 reported a seven-step synthesis (Scheme 1) for the γ-lactone intermediate. When chiral glyceraldehyde used as the starting material, two new chiral centers were generated following Witting reaction and dihydoxy-lation. After cyclic sulfonate formed, the fluoro subsititution was introduced stereospecifically by a SN2 reaction with HF-Et3N. Lactonization was achieved under the acid conditions followed by hydroxy protecting step to give the desired intermediate. The main disadvantage of this approach is that considerable quantities of both solid and acidic liquid wastes were produced during the process which is very difficult to handle with (e.x. filtration) and/or contributes to the environment pollution upon disposal.

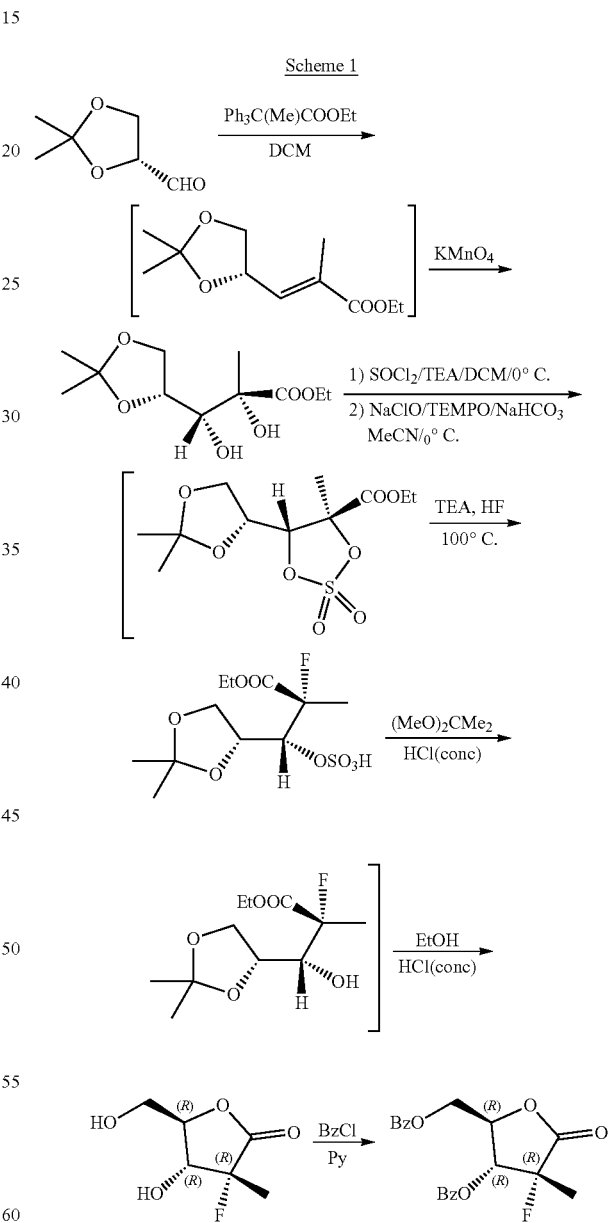

Scheme 1

In a similar process reported in CN105418547A (Scheme 2), the Witting product was epoxidized followed by ring-opening fluorolation by HF-Et$_3$N or other fluoro-containing reagents, significant amount of regioisomer was observed which was difficult to remove from the oily mixture.

Scheme 2

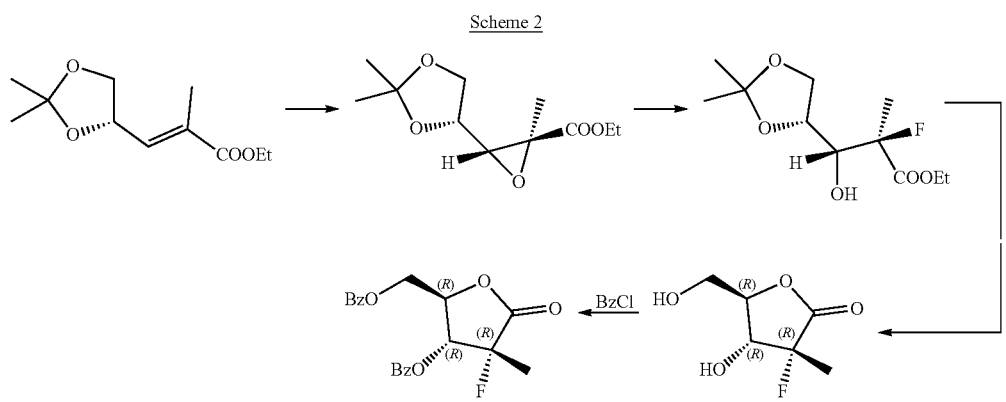

US20080145901 reported an enzymetic approach to the γ-lactone intermediate (scheme 3). Treatment of ethyl 2-fluoro-propinate with chiral glyceraldehyde to form the aldol adducts consisting the mixture of four disteroisomers. The disteroisomers were selectively hydrolyzed by enzyme and the major isomer was obtained. After lactonization and hydroxyl protecting, other two isomers were removed by recrystallization.

WO2008090046 reported a similar synthesis as described in Scheme 3. 2-fluoro-propionic acid was converted to different bulky ester or amide and reacted with chiral glyceraldehydes. The mixture of the disteroisomers were purified by recrystallization to obtain the pure isomer. By using the method described in Scheme 3, the γ-lactone can be scale up to kilogram quantities but the de value of the final product can not achieve desired level.

In WO2014108525, WO2014056442 and CN105111169, different auxiliaries were used in the Aldol Reaction to improve the disteroisomeric selectivity (Scheme 4). The process was shortened to 3-4 steps and the de value was increase significantly.

Scheme 4

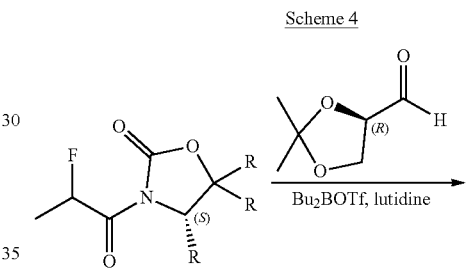

Scheme 3

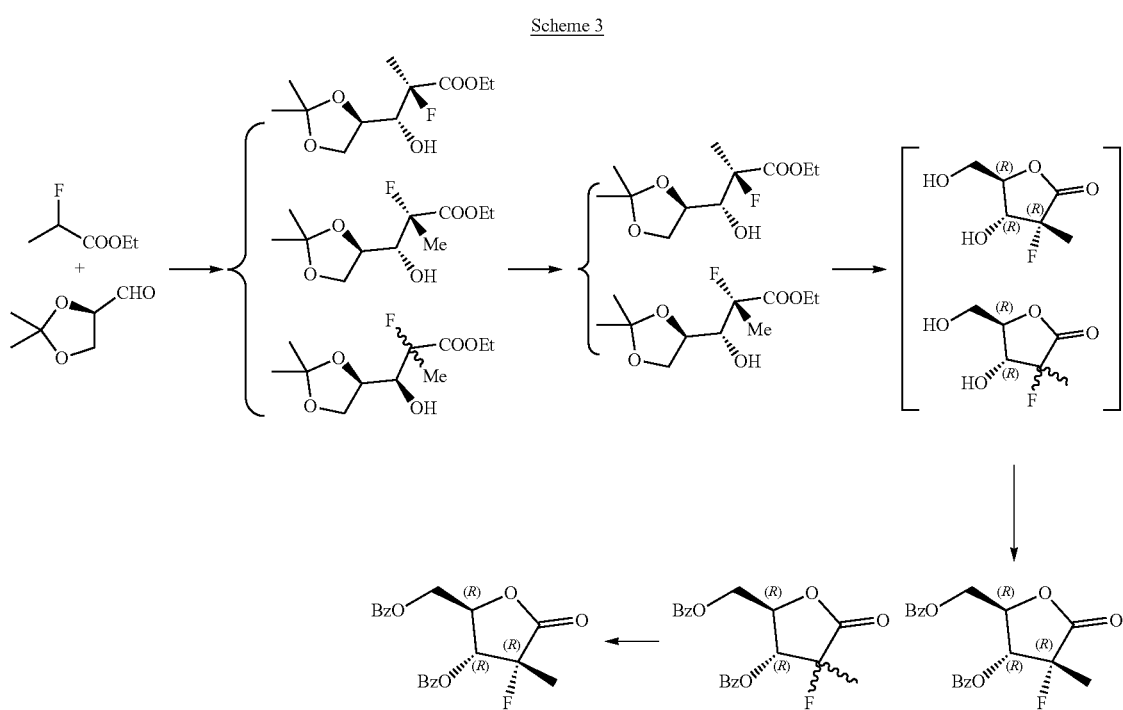

-continued

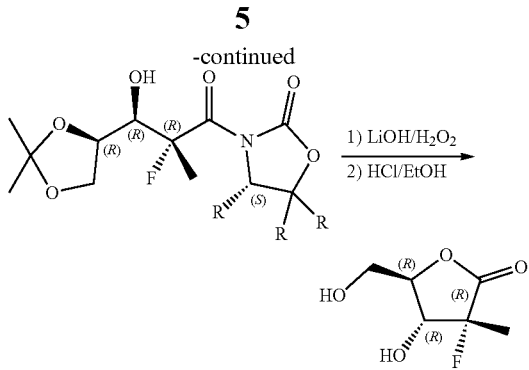

SUMMARY OF THE INVENTION

In one aspect, the present invention provides a process for preparing a compound of formula (VI):

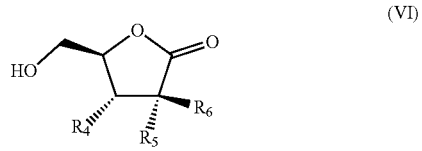

(VI)

wherein $R_4$, $R_5$, $R_6$ are each independently hydrogen, OH, halogen, or $C_{1-3}$ alkyl; or $R_5$ and $R_6$, together with the carbon to which they are adjacent to, form a $C_{3-5}$ cycloalkyl, the process comprising reacting a compound of formula (IV),

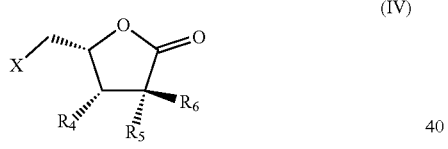

(IV)

wherein X is a leaving group selected from Cl, Br, I, nitrite, and a sulfonate of formula R—SO$_3$—;
R is methyl, trifluoromethyl, ethyl, phenyl, p-methyl-phenyl, m-methyl-phenyl, o-methyl-phenyl, or naphthalenyl; and
$R_4$, $R_5$, $R_6$ are defined as hereinabove;
with a base to provide the compound of formula (VI).

In another aspect, the present invention provides a process for protecting the hydroxyl group(s) of the compound of formula (VI) to prepare a compound of formula (VII),

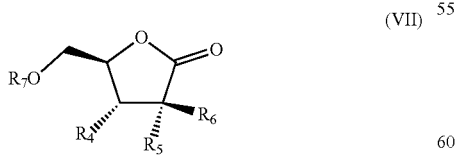

(VII)

wherein $R_7$ is a hydroxyl protecting group, and $R_4$, $R_5$, $R_6$ are defined as hereinabove, and if any one of $R_4$, $R_5$, $R_6$ is hydroxyl, then said hydroxyl is also protected as $OR_7$.

In yet another aspect, the present invention provides a process for preparing a compound of formula (IV):

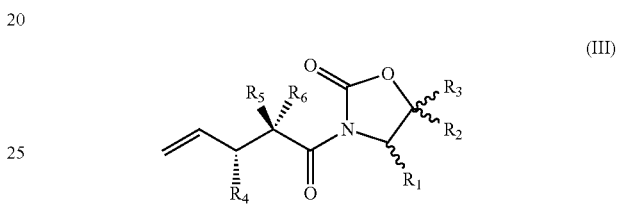

(IV)

wherein X is a leaving group selected from Cl, Br, I, nitrite, and a sulfonate of formula R—SO$_3$—;
R is methyl, trifluoromethyl, ethyl, phenyl, p-methyl-phenyl, m-methyl-phenyl, o-methyl-phenyl, or naphthalenyl; and
$R_4$, $R_5$, and $R_6$ are each independently hydrogen, OH, halogen, or $C_{1-3}$ alkyl; or $R_5$ and $R_6$, together with the carbon to which they are adjacent to, form a $C_{3-5}$ cycloalkyl,
the process comprising reacting a compound of formula (III),

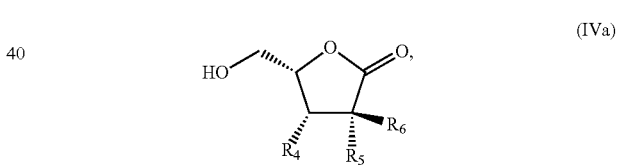

(III)

wherein $R_1$ is $C_{1-6}$ alkyl, phenyl or substituted phenyl, or benzyl or substituted benzyl; $R_2$ and $R_3$ are each independently hydrogen, $C_{1-6}$ alkyl, or phenyl or substituted phenyl; and $R_4$, $R_5$, and $R_6$ are defined as hereinabove,
(a) with a halogenating agent, to produce the compound of formula (IV), wherein X is Cl, Br, or I; or
(b) (i) with an oxidizing agent, to produce a compound of formula (IVa),

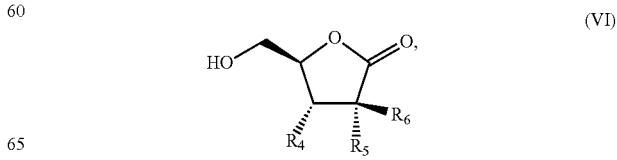

(IVa)

wherein $R_4$, $R_5$, $R_6$ are defined as hereinabove; and
(ii) further reacting the compound of formula (IVa) with a sulfonating agent to produce the compound of formula (IV), wherein X is a sulfonate of formula R—SO$_3$—, and R is as defined hereinabove, and
(iii) optionally reacting the compound of formula (IV), wherein X is a sulfonate of formula R—SO$_3$—, and R is as defined hereinabove, with an alkali salt of nitrite, to produce the compound of formula (IV), wherein X is nitrite.

In yet another aspect, the present invention provides a process for preparing a compound of formula (VI):

(VI)

wherein R₄, R₅, R₆ are each independently hydrogen, OH, halogen, or $C_{1-3}$ alkyl; or R₅ and R₆, together with the carbon to which they are adjacent to, form a $C_{3-5}$ cycloalkyl, the process comprising:
(A) reacting a compound of formula (III),

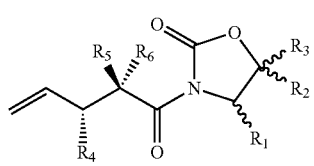
(III)

wherein R₁ is $C_{1-6}$ alkyl, phenyl or substituted phenyl, or benzyl or substituted benzyl;

R₂ and R₃ are each independently hydrogen, $C_{1-6}$ alkyl, or phenyl or substituted phenyl; and R₄, R₅, and R₆ are defined as hereinabove, a) with a halogenating agent, to produce the compound of formula (IV),

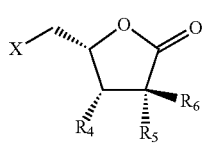
(IV)

wherein X is Cl, Br, or I; or
b) (i) with an oxidizing agent, to produce a compound of formula (IVa),

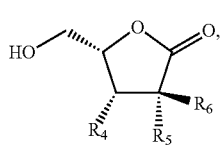
(IVa)

wherein R₄, R₅, R₆ are defined as hereinabove;
(ii) further reacting the compound of formula (IVa) with a sulfonating agent to produce the compound of formula (IV), wherein X is a sulfonate of formula R—SO₃—, and R is methyl, trifluoromethyl, ethyl, phenyl, p-methyl-phenyl, m-methyl-phenyl, o-methyl-phenyl, or naphthalenyl; and
(iii) optionally reacting the compound of formula (IV), wherein X is a sulfonate of formula R—SO₃—, and R is defined hereinabove, with an alkali salt of nitrite, to produce a compound of formula (IV), wherein X is nitrite.
(B) reacting the compound of formula (IV), wherein X is a leaving group selected from Cl, Br, I, nitrite, and a sulfonate of formula R—SO₃—; R is methyl, trifluoromethyl, ethyl, phenyl, p-methyl-phenyl, m-methyl-phenyl, o-methyl-phenyl, or naphthalenyl; and R₄, R₅, and R₆ are each independently hydrogen, OH, halogen, or $C_{1-3}$ alkyl; or R₅ and R₆, together with the carbon to which they are adjacent to, form a $C_{3-5}$ cycloalkyl, with a base to produce compound of formula (VI).

In a further aspect, the present invention provides a compound of formula (IV),

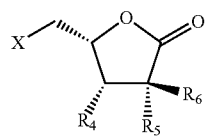
(IV)

wherein X is a leaving group selected from Cl, Br, I, nitrite, and a sulfonate of formula R—SO₃—;

R is methyl, trifluoromethyl, ethyl, phenyl, p-methyl-phenyl, m-methyl-phenyl, o-methyl-phenyl, or naphthalenyl; and R₄, R₅, R₆ are each independently hydrogen, OH, halogen, or $C_{1-3}$ alkyl; or R₅ and R₆, together with the carbon to which they are adjacent to, form a $C_{3-5}$ cycloalkyl.

In yet another aspect, the present invention provides a compound of formula (III),

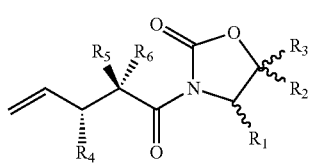
(III)

wherein R₁ is $C_{1-6}$ alkyl, phenyl or substituted phenyl, or benzyl or substituted benzyl;

R₂ and R₃ are each independently hydrogen, $C_{1-6}$ alkyl, or phenyl or substituted phenyl;

R₄, R₅, R₆ are each independently hydrogen, OH, halogen, or $C_{1-3}$ alkyl; or R₅ and R₆, together with the carbon to which they are adjacent to, form a $C_{3-5}$ cycloalkyl.

DETAILED DESCRIPTION OF THE INVENTION

In one aspect, the present invention provides a process for preparing a compound of formula (VI):

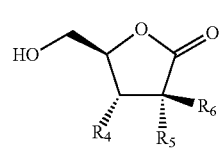
(VI)

wherein R₄, R₅, R₆ are each independently hydrogen, OH, halogen, or $C_{1-3}$ alkyl; or R₅ and R₆, together with the carbon to which they are adjacent to, form a $C_{3-5}$ cycloalkyl, the process comprising reacting a compound of formula (IV),

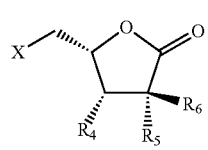
(IV)

wherein X is a leaving group selected from Cl, Br, I, nitrite, and a sulfonate of formula R—SO₃—;

R is methyl, trifluoromethyl, ethyl, phenyl, p-methyl-phenyl, m-methyl-phenyl, o-methyl-phenyl, or naphthalenyl; and $R_4$, $R_5$, $R_6$ are defined as hereinabove;

with a base to provide the compound of formula (VI).

Without being bound by any theory, it is believed that the conversion from the compound of formula (IV) to the compound of formula (VI) is achieved via a base-catalyzed rearrangement.

In certain embodiments, the base is selected from an alkali hydroxide, an alkali carbonate, an alkali phosphate, an alkali alkoxide, and mixtures thereof. In certain embodiments, an alkali hydroxide is selected from LiOH, NaOH, KOH, and CsOH. In certain embodiments, an alkali carbonate is selected from $Na_2CO_3$, $K_2CO_3$, and $Cs_2CO_3$. In certain embodiments, an alkali phosphate is selected from $Na_3PO_4$ and $K_3PO_4$. In certain embodiments, an alkali alkoxide is an alkali $C_{1-4}$ alkoxide. Examples of an alkali alkoxide includes, but not limited to, NaOMe, KOMe, NaOEt, KOEt, isopropyl-ONa, isopropyl-OK, and t-BuONa, and t-BuOK. The reaction can be carried out in a variety of medium, including but not limited to, water, alcohol (e.g., MeOH, EtOH, i-PrOH), ether-like solvent (e.g., ether, THF, 2-Me-THF, Dioxane), and mixtures thereof.

In certain embodiments, the step of reacting the compound of formula (IV) with a base is followed by treatment with an acid. In certain embodiments, the acid is a proton acid such as HCl, $H_2SO_4$, $H_3PO_4$, poly-phosphoric acid, p-toluenesulfonic acid, $C_{1-4}$alkyl-COOH (e.g., $CH_3COOH$), and mixtures thereof. In certain other embodiments, the acid is an acidic resin or acidic ion-exchange resin.

In certain embodiments, $R_4$ is OH. In certain embodiments, $R_5$ and $R_6$ are each independently OH, halogen or $C_{1-3}$ alkyl. In certain other embodiments, $R_5$ and $R_6$, together with the carbon to which they are adjacent to, form a $C_{3-5}$ cycloalkyl. In certain embodiments, $R_5$ is fluorine, and $R_6$ is methyl.

In certain embodiments, X is Cl. In certain other embodiments, X is Br. In yet other embodiments, X is I.

In certain embodiments, X is a sulfonate of formula $R—SO_3—$, wherein R is methyl, trifluoromethyl, ethyl, phenyl, p-methyl-phenyl, m-methyl-phenyl, o-methyl-phenyl, or naphthalenyl. In certain other embodiments, X is mesylate. In yet other embodiments, X is tosylate. In yet other embodiments, X is naphthalenyl sulfonate. In yet other embodiments, X is nitrite.

In another aspect, the present invention provides a process for protecting the hydroxyl group(s) of the compound of formula (VI) to prepare a compound of formula (VII),

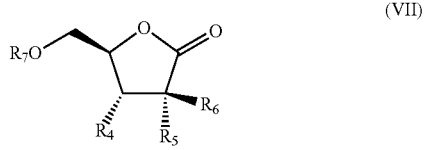

(VII)

wherein $R_7$ is a hydroxyl protecting group, and $R_4$, $R_5$, $R_6$ are defined as hereinabove, and if any one of $R_4$, $R_5$, $R_6$ is hydroxyl, then said hydroxyl is also protected as $OR_7$. Suitable hydroxyl protecting groups can be found in Greene and Wuts, Protective Groups in Organic Synthesis, 3$^{rd}$ Ed., 1999, which is incorporated by reference in its entirety. In certain embodiments, $R_7$ is benzyl, p-methoxybenzyl (PMB), benzyloxy methyl, p-methoxybenzyloxy methyl, ($C_1$-$C_4$)alkyl-acyl (e.g., acetyl), halogen substituted ($C_1$-$C_4$) alkyl-acyl (e.g., chloroacetyl, dichloroacetyl, trichloroacetyl, and trifluoroacetyl), aryl-acyl (e.g., benzoyl), trimethylsilylethoxymethyl (SEM), silyl protecting groups (e.g., trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl, di-t-butylmethylsilyl, tris(trimethylsilyl)silyl, (2-hydroxystyryl)dimethylsilyl, 2-hydroxystyryl)disopropylsilyl, t-butylmethoxyphenylsilyl, t-butoxydiphenylsilyl), allyloxycarbonyl (alloc, $—C(O)O—CH=CH_2$), or t-butoxylmethyl.

In certain embodiments, $R_7$ is $C_{1-4}$ alkyl-C(=O)—, optionally substituted phenyl-C(=O)—, or optionally substituted benzyl. In certain other embodiments, $R_7$ is acetyl or benzoyl.

In yet another aspect, the present invention provides a process for preparing a compound of formula (IV):

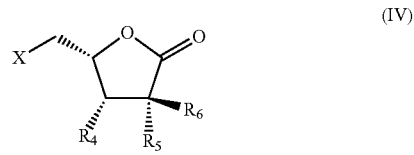

(IV)

wherein X is a leaving group selected from Cl, Br, I, nitrite, and a sulfonate of formula $R—SO_3—$;

R is methyl, trifluoromethyl, ethyl, phenyl, p-methyl-phenyl, m-methyl-phenyl, o-methyl-phenyl, or naphthalenyl; and $R_4$, $R_5$, and $R_6$ are each independently hydrogen, OH, halogen, or $C_{1-3}$ alkyl; or $R_5$ and $R_6$, together with the carbon to which they are adjacent to, form a $C_{3-5}$ cycloalkyl, the process comprising reacting a compound of formula (III),

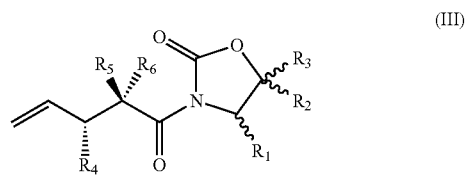

(III)

wherein $R_1$ is $C_{1-6}$ alkyl, phenyl or substituted phenyl, or benzyl or substituted benzyl;

$R_2$ and $R_3$ are each independently hydrogen, $C_{1-6}$ alkyl, or phenyl or substituted phenyl; and $R_4$, $R_5$, and $R_6$ are defined as hereinabove, (a) with a halogenating agent, to produce the compound of formula (IV), wherein X is Cl, Br, or I; or (b) (i) with an oxidizing agent, to produce a compound of formula (IVa),

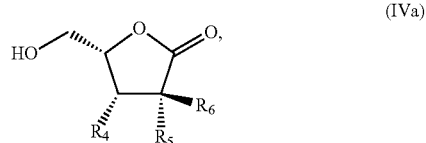

(IVa)

wherein $R_4$, $R_5$, $R_6$ are defined as hereinabove; and
(ii) further reacting the compound of formula (IVa) with a sulfonating agent to produce the compound of formula (IV), wherein X is a sulfonate of formula $R-SO_3-$, and R is as defined hereinabove, and
(iii) optionally reacting the compound of formula (IV), wherein X is a sulfonate of formula $R-SO_3-$, and R is as defined hereinabove, with an alkali salt of nitrite, to produce the compound of formula (IV), wherein X is nitrite.

In certain embodiments, the halogenating agent is selected from $Cl_2$, N-Chlorosuccinimide (NCS), 1,3-Dichloro-5,5-dimethylhydantoin, 1-Bromo-3-chloro-5,5-dimethylhydantoin, $Br_2$, N-Bromosuccinimide (NBS), 1,3-Dibromo-5,5-dimethylhydantoin, $I_2$, N-Iodosuccinimide (NIS), and 1,3-Diiodo-5,5-dimethylhydantoin.

In certain embodiments, the oxidizing agent is selected from hydrogen peroxide, m-chloroperbenzoic acid, t-BuOOH, or $CF_3COOOH$.

In certain embodiments, the sulfonating agent is a compound of formula $R-SO_3-Y$, wherein Y is leaving group such as Cl or Br, and R is methyl, trifluoromethyl, ethyl, phenyl, p-methyl-phenyl, m-methyl-phenyl, o-methyl-phenyl, or naphthalenyl.

In certain embodiments, the alkali salt of nitrite is sodium nitrite or patasium nitrite.

In yet another aspect, the present invention provides a process for preparing a compound of formula (VI):

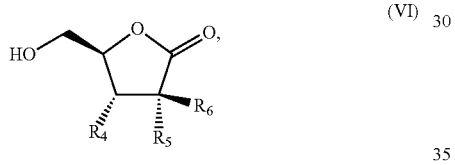
(VI)

wherein $R_4$, $R_5$, $R_6$ are each independently hydrogen, OH, halogen, or $C_{1-3}$ alkyl; or $R_5$ and $R_6$, together with the carbon to which they are adjacent to, form a $C_{3-5}$ cycloalkyl,
the process comprising:
(A) reacting a compound of formula (III),

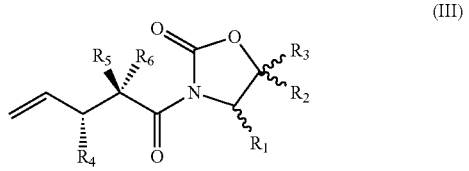
(III)

wherein $R_1$ is $C_{1-6}$ alkyl, phenyl or substituted phenyl, or benzyl or substituted benzyl;
$R_2$ and $R_3$ are each independently hydrogen, $C_{1-6}$ alkyl, or phenyl or substituted phenyl; and $R_4$, $R_5$, and $R_6$ are defined as hereinabove,
(a) with a halogenating agent, to produce the compound of formula (IV),

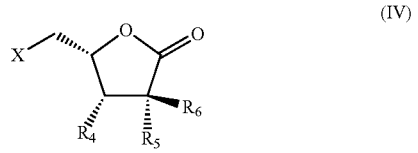
(IV)

wherein X is Cl, Br, or I; or
(b) (i) with an oxidizing agent, to produce a compound of formula (IVa),

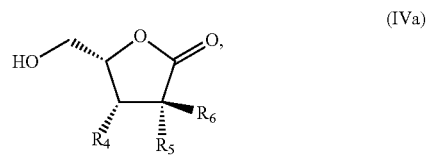
(IVa)

wherein $R_4$, $R_5$, $R_6$ are defined as hereinabove;
(ii) further reacting the compound of formula (IVa) with a sulfonating agent to produce the compound of formula (IV), wherein X is a sulfonate of formula $R-SO_3-$, and R is methyl, trifluoromethyl, ethyl, phenyl, p-methyl-phenyl, m-methyl-phenyl, o-methyl-phenyl, or naphthalenyl; and
(iii) optionally reacting the compound of formula (IV), wherein X is a sulfonate of formula $R-SO_3-$, and R is defined hereinabove, with an alkali salt of nitrite, to produce a compound of formula (IV), wherein X is nitrite;
(B) reacting the compound of formula (IV), wherein X is a leaving group selected from Cl, Br, I, nitrite, and a sulfonate of formula $R-SO_3-$; R is methyl, trifluoromethyl, ethyl, phenyl, p-methyl-phenyl, m-methyl-phenyl, o-methyl-phenyl, or naphthalenyl; and $R_4$, $R_5$, and $R_6$ are each independently hydrogen, OH, halogen, or $C_{1-3}$ alkyl; or $R_5$ and $R_6$, together with the carbon to which they are adjacent to, form a $C_{3-5}$ cycloalkyl, with a base to produce compound of formula (VI).

In certain embodiments, the halogenating agent is selected from $Cl_2$, N-Chlorosuccinimide (NCS), 1,3-Dichloro-5,5-dimethylhydantoin, 1-Bromo-3-chloro-5,5-dimethylhydantoin, $Br_2$, N-Bromosuccinimide (NBS), 1,3-Dibromo-5,5-dimethylhydantoin, $I_2$, N-Iodosuccinimide (NIS), and 1,3-Diiodo-5,5-dimethylhydantoin.

In certain embodiments, the oxidizing agent is selected from hydrogen peroxide, m-chloroperbenzoic acid, t-BuOOH, or $CF_3COOOH$.

In certain embodiments, the sulfonating agent is a compound of formula $R-SO_3-Y$, wherein Y is leaving group such as Cl or Br and R is methyl, trifluoromethyl, ethyl, phenyl, p-methyl-phenyl, m-methyl-phenyl, o-methyl-phenyl, or naphthalenyl.

In certain embodiments, the alkali salt of nitrite is sodium nitrite or patasium nitrite.

In certain embodiments, the base used in Step (B) is selected from an alkali hydroxide, an alkali carbonate, an alkali phosphate, an alkali alkoxide, and mixtures thereof. In certain embodiments, an alkali hydroxide is selected from LiOH, NaOH, KOH, and CsOH. In certain embodiments, an alkali carbonate is selected from $Na_2CO_3$, $K_2CO_3$, and $Cs_2CO_3$. In certain embodiments, an alkali phosphate is selected from $Na_3PO_4$ and $K_3PO_4$. In certain embodiments, an alkali alkoxide is an alkali $C_{1-4}$ alkoxide. Examples of an alkali alkoxide includes, but not limited to, NaOMe, KOMe, NaOEt, KOEt, isopropyl-ONa, isopropyl-OK, and t-BuONa, and t-BuOK. The reaction can be carried out in a variety of medium, including but not limited to, water, alcohol (e.g., MeOH, EtOH, i-PrOH), ether-like solvent (e.g., ether, THF, 2-Me-THF, Dioxane), and mixtures thereof.

In certain embodiments, the step of reacting the compound of formula (IV) with a base is followed by treatment with an acid. In certain embodiments, the acid is a proton acid such as HCl, H$_2$SO$_4$, H$_3$PO$_4$, poly-phosphoric acid, p-toluenesulfonic acid, C$_{1-4}$ alkyl-COOH (e.g., CH$_3$COOH), and mixtures thereof. In certain other embodiments, the acid is an acidic resin or acidic ion-exchange resin.

In certain embodiments, R$_4$ is OH. In certain embodiments, R$_5$ and R$_6$ are each independently OH, halogen or C$_{1-3}$ alkyl. In certain other embodiments, R$_5$ and R$_6$, together with the carbon to which they are adjacent to, form a C$_{3-5}$ cycloalkyl. In certain embodiments, R$_5$ is fluorine, and R$_6$ is methyl.

In certain embodiments, X is Cl. In certain other embodiments, X is Br. In yet other embodiments, X is I.

In certain embodiments, X is a sulfonate of formula R—SO$_3$—, wherein R is methyl, trifluoromethyl, ethyl, phenyl, p-methyl-phenyl, m-methyl-phenyl, o-methyl-phenyl, or naphthalenyl. In certain other embodiments, X is mesylate. In yet other embodiments, X is tosylate. In yet other embodiments, X is naphthalenyl sulfonate. In yet other embodiments, X is nitrite.

In a further aspect, the present invention provides a compound of formula (IV),

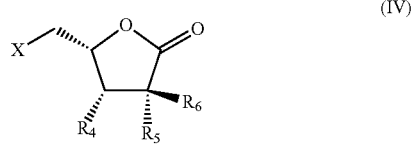

(IV)

wherein X is a leaving group selected from Cl, Br, I, nitrite, and a sulfonate of formula R—SO$_3$—;

R is methyl, trifluoromethyl, ethyl, phenyl, p-methylphenyl, m-methyl-phenyl, o-methyl-phenyl, or naphthalenyl; and R$_4$, R$_5$, R$_6$ are each independently hydrogen, OH, halogen, or C$_{1-3}$ alkyl; or R$_5$ and R$_6$, together with the carbon to which they are adjacent to, form a C$_{3-5}$ cycloalkyl.

In certain embodiments, X is Cl, Br or I. In certain other embodiments, X is mesylate or tosylate.

In certain embodiments, R$_4$ is OH, R$_5$ is fluorine, and R$_6$ is methyl.

In certain embodiments, the compound of formula (IV) is a compound selected from the following structures:

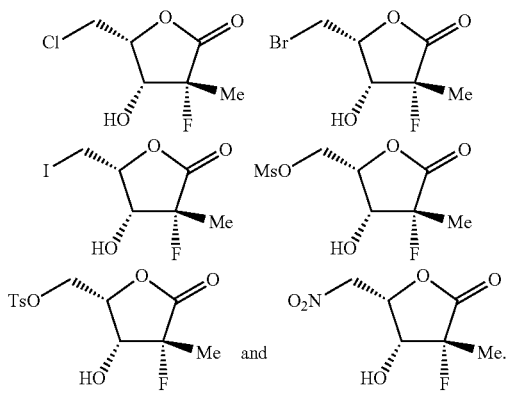

In yet another aspect, the present invention provides a compound of formula (III),

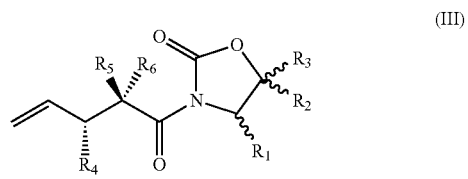

(III)

wherein R$_1$ is C$_{1-6}$ alkyl, phenyl or substituted phenyl, or benzyl or substituted benzyl;

R$_2$ and R$_3$ are each independently hydrogen, C$_{1-6}$ alkyl, or phenyl or substituted phenyl;

R$_4$, R$_5$, R$_6$ are each independently hydrogen, OH, halogen, or C$_{1-3}$ alkyl; or R$_5$ and R$_6$, together with the carbon to which they are adjacent to, form a C$_{3-5}$ cycloalkyl.

In certain embodiments, R$_1$ is (R)-isopropyl, (S)-isopropyl, (R)-t-butyl, (S)-t-butyl, (R)-benzyl, (S)-benzyl, (R)-phenyl, or (S)-phenyl. In certain embodiments, R$_4$ is OH, R$_5$ is fluorine, and R$_6$ is methyl.

In certain embodiments, the compound of formula (III) is a compound selected from the following structures:

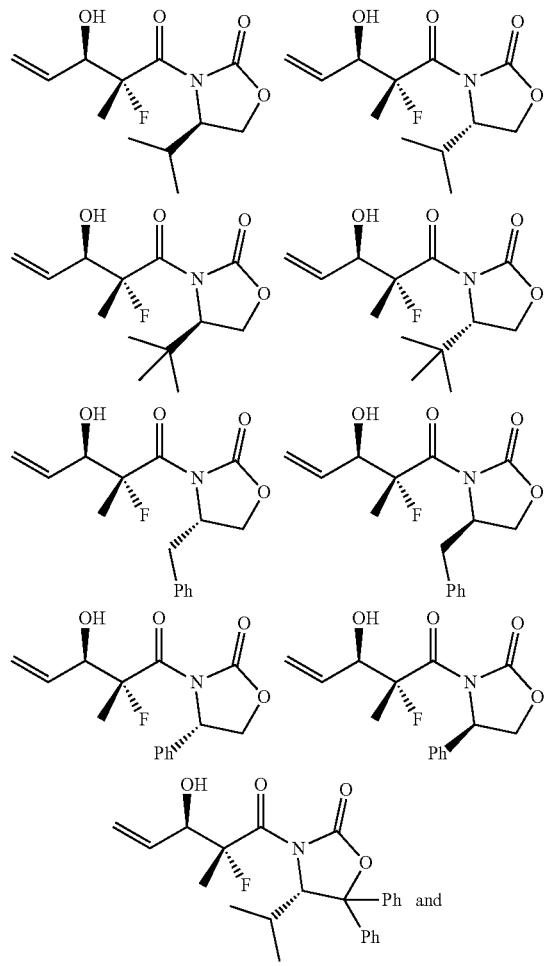

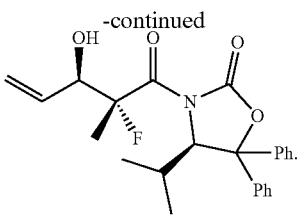

In yet another aspect, the present invention provides a compound having the structure of:

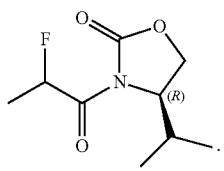

Definitions

As used in the specification and claims, the singular form "a", "an" and "the" includes plural references unless the context clearly dictates otherwise.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this disclosure.

Definitions of specific functional groups and chemical terms are described in more detail below. The chemical elements are identified in accordance with the Periodic Table of the Elements, CAS version, Handbook of Chemistry and Physics, 75th ed., inside cover, and specific functional groups are generally defined as described therein. Additionally, general principles of organic chemistry, as well as specific functional moieties and reactivity, are described in *Organic Chemistry*, Thomas Sorrell, University Science Books, Sansalito, 1999; Smith and March *March's Advanced Organic Chemistry*, 5th ed., John Wiley & Sons, Inc., NewYork, 2001; Larock, *Comprehensive Organic Transformations*, VCH Publishers, Inc., NewYork, 1989; and Carruthers, *Some Modern Methods of Organic Synthesis*, 3rd ed., Cambridge University Press, Cambridge, 1987.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, the term "alkali" refers to any of the elements of lithium, sodium, potassium, rubidium, cesium, and francium, occupying Group IA (1) of the periodic table. In certain embodiments, an alkali is selected from lithium, sodium, potassium, and cesium.

As used herein, the term "alkyl" refers to a straight or branched hydrocarbon chain radical consisting solely of carbon and hydrogen atoms, containing no unsaturation, having from one to ten carbon atoms (e.g., $C_{1-10}$ alkyl). Whenever it appears herein, a numerical range such as "1 to 10" refers to each integer in the given range; e.g., "1 to 10 carbon atoms" means that the alkyl group can consist of 1 carbon atom, 2 carbon atoms, 3 carbon atoms, etc., up to and including 10 carbon atoms, although the present definition also covers the occurrence of the term "alkyl" where no numerical range is designated. In some embodiments, "alkyl" can be a $C_{1-6}$ alkyl group. In some embodiments, alkyl groups have 1 to 10, 1 to 8, 1 to 6, or 1 to 3 carbon atoms. Representative saturated straight chain alkyls include, but are not limited to, -methyl, -ethyl, -n-propyl, -n-butyl, -n-pentyl, and -n-hexyl; while saturated branched alkyls include, but are not limited to, -isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, and the like. The alkyl is attached to the parent molecule by a single bond. Unless stated otherwise in the specification, an alkyl group is optionally substituted by one or more of substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si(R$^a$)$_3$, —OR$^a$, —SR$^a$, —OC(O)—R$^a$, —N(R$^a$)$_2$, —C(O)R$_a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S(O)$_t$N(R$^a$)$_2$ (where t is 1 or 2), —P(=O)(R$^a$)(R$^a$), or —O—P(=O)(OR$^a$)$_2$ where each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein. In a non-limiting embodiment, a substituted alkyl can be selected from fluoromethyl, difluoromethyl, trifluoromethyl, 2-fluoroethyl, 3-fluoropropyl, hydroxymethyl, 2-hydroxyethyl, 3-hydroxypropyl, benzyl, and phenethyl.

As used herein, the term "perhaloalkyl" refers to an alkyl group in which all of the hydrogen atoms have been replaced with a halogen selected from fluoro, chloro, bromo, and iodo. In some embodiments, all of the hydrogen atoms are each replaced with fluoro. In some embodiments, all of the hydrogen atoms are each replaced with chloro. Examples of perhaloalkyl groups include —CF$_3$, —CF$_2$CF$_3$, —CF$_2$CF$_2$CF$_3$, —CFCl$_2$, —CF$_2$Cl and the like.

As used herein, the term "acyl" refers to R—C(O)— groups such as, but not limited to, (alkyl)-C(O)—, (alkenyl)-C(O)—, (alkynyl)-C(O)—, (aryl)-C(O)—, (cycloalkyl)-C(O)—, (heteroaryl)-C(O)—, (heteroalkyl)-C(O)—, and (heterocycloalkyl)-C(O)—, wherein the group is attached to the parent molecular structure through the carbonyl functionality. In some embodiments, it is a $C_{1-10}$ acyl radical which refers to the total number of chain or ring atoms of the, for example, alkyl, alkenyl, alkynyl, aryl, cyclohexyl, heteroaryl or heterocycloalkyl portion plus the carbonyl carbon of acyl. For example, a $C_4$-acyl has three other ring or chain atoms plus carbonyl. If the R radical is heteroaryl or heterocycloalkyl, the hetero ring or chain atoms contribute to the total number of chain or ring atoms. Unless stated otherwise in the specification, the "R" of an acyloxy group can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —O$R^a$, —S$R^a$, —OC(O)—$R^a$, —N($R^a$)$_2$, —C(O)$R_a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t$N($R^a$)$_2$ (where t is 1 or 2), —P(=O)($R^a$)($R^a$), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

As used herein, the terms "aromatic" or "aryl" refer to a radical with 6 to 14 ring atoms (e.g., $C_{6-14}$ aromatic or $C_{6-14}$ aryl) which has at least one ring having a conjugated pi electron system which is carbocyclic (e.g., phenyl, fluorenyl, and naphthyl). In some embodiments, the aryl is a $C_{6-10}$ aryl group. For example, bivalent radicals formed from substituted benzene derivatives and having the free valences at ring atoms are named as substituted phenylene radicals. In other embodiments, bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 14 aryl" refers to each integer in the given range; e.g., "6 to 14 ring atoms" means that the aryl group can consist of 6 ring atoms, 7 ring atoms, etc., up to and including 14 ring atoms. The term includes monocyclic or fused-ring polycyclic (i.e., rings which share adjacent pairs of ring atoms) groups. Polycyclic aryl groups include bicycles, tricycles, tetracycles, and the like. In a multi-ring group, only one ring is required to be aromatic, so groups such as indanyl are encompassed by the aryl definition. Non-limiting examples of aryl groups include phenyl, phenalenyl, naphthalenyl, tetrahydronaphthyl, phenanthrenyl, anthracenyl, fluorenyl, indolyl, indanyl, and the like. Unless stated otherwise in the specification, an aryl moiety can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —O$R^a$, —S$R^a$, —OC(O)—$R^a$, —N($R^a$)$_2$, —C(O)$R_a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t$N($R^a$)$_2$ (where t is 1 or 2), —P(=O)($R^a$)($R^a$), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

As used herein, the term "cycloalkyl" refers to a monocyclic or polycyclic radical that contains only carbon and hydrogen, and can be saturated or partially unsaturated. Partially unsaturated cycloalkyl groups can be termed "cycloalkenyl" if the carbocycle contains at least one double bond, or "cycloalkynyl" if the carbocycle contains at least one triple bond. Cycloalkyl groups include groups having from 3 to 13 ring atoms (i.e., $C_{3-13}$ cycloalkyl). Whenever it appears herein, a numerical range such as "3 to 10" refers to each integer in the given range; e.g., "3 to 13 carbon atoms" means that the cycloalkyl group can consist of 3 carbon atoms, 4 carbon atoms, 5 carbon atoms, etc., up to and including 13 carbon atoms. The term "cycloalkyl" also includes bridged and spiro-fused cyclic structures containing no heteroatoms. The term also includes monocyclic or fused-ring polycyclic (i.e., rings which share adjacent pairs of ring atoms) groups. Polycyclic aryl groups include bicycles, tricycles, tetracycles, and the like. In some embodiments, "cycloalkyl" can be a $C_{3-8}$ cycloalkyl radical. In some embodiments, "cycloalkyl" can be a $C_{3-5}$ cycloalkyl radical. Illustrative examples of cycloalkyl groups include, but are not limited to the following moieties: $C_{3-6}$ carbocyclyl groups include, without limitation, cyclopropyl ($C_3$), cyclobutyl ($C_4$), cyclopentyl ($C_5$), cyclopentenyl ($C_5$), cyclohexyl ($C_6$), cyclohexenyl ($C_6$), cyclohexadienyl ($C_6$) and the like. Examples of $C_{3-7}$ carbocyclyl groups include norbornyl ($C_7$). Examples of $C_{3-8}$ carbocyclyl groups include the aforementioned $C_{3-7}$ carbocyclyl groups as well as cycloheptyl($C_7$), cycloheptadienyl ($C_7$), cycloheptatrienyl ($C_7$), cyclooctyl ($C_8$), bicyclo[2.2.1]heptanyl, bicyclo[2.2.2]octanyl, and the like. Examples of $C_{3-13}$ carbocyclyl groups include the aforementioned $C_{3-8}$ carbocyclyl groups as well as octahydro-1H indenyl, decahydronaphthalenyl, spiro[4.5]decanyl and the like. Unless stated otherwise in the specification, a cycloalkyl group can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —O$R^a$, —S$R^a$, —OC(O)—$R^a$, —N($R^a$)$_2$, —C(O)$R_a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t$N($R^a$)$_2$ (where t is 1 or 2), —P(=O)($R^a$)($R^a$), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein. The terms "cycloalkenyl" and "cycloalkynyl" mirror the above description of "cycloalkyl" wherein the prefix "alk" is replaced with "alken" or "alkyn" respectively, and the parent "alkenyl" or "alkynyl" terms are as described herein. For example, a cycloalkenyl group can have 3 to 13 ring atoms, such as 5 to 8 ring atoms. In some embodiments, a cycloalkynyl group can have 5 to 13 ring atoms.

As used herein, the term "ether" refers to a —O—$R^b$—O— radical where each $R^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein.

As used herein, the term "halo", "halide", or, alternatively, "halogen" means fluoro, chloro, bromo or iodo. The terms "haloalkyl," "haloalkenyl," "haloalkynyl" and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine, such as, but not limited to, trifluoromethyl, difluoromethyl, 2,2,2-trifluoroethyl, 1-fluoromethyl-2-fluoroethyl, and the like. Each of the alkyl, alkenyl, alkynyl and alkoxy groups are as defined herein and can be optionally further substituted as defined herein.

Where substituent groups are specified by their conventional chemical Formulae, written from left to right, they equally encompass the chemically identical substituents that would result from writing the structure from right to left, e.g., —CH$_2$O— is equivalent to —OCH$_2$—.

As used herein, the term "leaving group or atom" refers any group or atom that will, under the reaction conditions, cleave from the starting material, thus promoting reaction at a specified site. Suitable non-limiting examples of such groups unless otherwise specified include halogen atoms, mesyloxy, p-nitrobenzensulphonyloxy, trifluoromethyloxy, and tosyloxy groups.

As used herein, the term "protecting group" has the meaning conventionally associated with it in organic synthesis, i.e., a group that selectively blocks one or more reactive sites in a multifunctional compound such that a chemical reaction can be carried out selectively on another unprotected reactive site and such that the group can readily be removed after the selective reaction is complete. Non-limiting embodiments of functional groups that can be masked with a protecting group include an amine, hydroxy, thiol, carboxylic acid, and aldehyde. For example, a hydroxy protected form is where at least one of the hydroxy groups present in a compound is protected with a hydroxy protecting group. A variety of protecting groups are disclosed, for example, in T. H. Greene and R G. M. Wuts, *Protective Groups in Organic Synthesis*, Third Edition, John Wiley & Sons, New York (1999), incorporated herein by reference in its entirety. For additional background information on protecting group methodologies (materials, methods and strategies for protection and deprotection) and other synthetic chemistry transformations useful in producing the compounds described herein, see in R. Larock, Comprehensive organic Transformations, VCH Publishers (1989); T. W. Greene and P. G. M. Wuts, Protective Groups in Organic Synthesis, 3rd. Ed., John Wiley and Sons (1999); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995). These references are incorporated herein by reference in their entirety.

As used herein, the terms "substituted" or "substitution" mean that at least one hydrogen present on a group atom (e.g., a carbon or nitrogen atom) is replaced with a permissible substituent, e.g., a substituent which upon substitution for the hydrogen results in a stable compound, e.g., a compound which does not spontaneously undergo transformation such as by rearrangement, cyclization, elimination, or other reaction. Unless otherwise indicated, a "substituted" group can have a substituent at one or more substitutable positions of the group, and when more than one position in any given structure is substituted, the substituent is either the same or different at each position. Substituents include one or more group(s) individually and independently selected from acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfona-midyl, sulfoxyl, sulfonate, urea, —Si(R$^a$)$_3$, —OR$^a$, —SR$^a$, —OC(O)—R$^a$, —N(R$^a$)$_2$, —C(O)R$_a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)$_t$N(R$^a$)$_2$ (where t is 1 or 2), —P(=O)(R$^a$)(R$^a$), or —O—P(=O)(OR$^a$)$_2$ where each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein. For example, a cycloalkyl substituent can have a halide substituted at one or more ring carbons, and the like. The protecting groups that can form the protective derivatives of the above substituents are known to those of skill in the art and can be found in references such as Greene and Wuts, above.

Suitable substituents include, but are not limited to, haloalkyl and trihaloalkyl, alkoxyalkyl, halophenyl, -M-heteroaryl, -M-heterocycle, -M-aryl, -M-OR$^a$, -M-SR$^a$, -M-N(R$^a$)$_2$, -M-OC(O)N(R$^a$)$_2$, -M-C(=NR$^a$)N(R$^a$)$_2$, -M-C(=NR$^a$)OR$^a$, -M-P(O)(R$^a$)$_2$, Si(R$^a$)$_3$, -M-NR$^a$C(O)R$^a$, -M-NR$^a$C(O)OR$^a$, -M-C(O)R$^a$, -M-C(=S)R$^a$, -M-C(=S)NR$^a$R$^a$, -M-C(O)N(R$^a$)$_2$, -M-C(O)NR$^a$-M-N(R$^a$)$_2$, -M-NR$^a$C(NR$^a$)N(R$^a$)$_2$, -M-NR$^a$C(S)N(R$^a$)$_2$, -M-S(O)$_2$R$^a$, -M C(O)R$^a$, -M-OC(O)R$^a$, -MC(O)SR$^a$, -M-S(O)$_2$N(R$^a$)$_2$, —C(O)-M-C(O)R$^a$, -MCO$_2$R$^a$, -MC(=O)N(R$^a$)$_2$, -M-C(=NH)N(R$^a$)$_2$, and -M-OC(=NH)N(R$^a$)$_2$ (wherein M is a C$_{1-6}$ alkyl group).

When a ring system (e.g., cycloalkyl, heterocyclyl, aryl, or heteroaryl) is substituted with a number of substituents varying within an expressly defined range, it is understood that the total number of substituents does not exceed the normal available valencies under the existing conditions. Thus, for example, a phenyl ring substituted with "p" substituents (where "p" ranges from 0 to 5) can have 0 to 5 substituents, whereas it is understood that a pyridinyl ring substituted with "p" substituents has a number of substituents ranging from 0 to 4. The maximum number of substituents that a group in the disclosed compounds can have can be easily determined. The substituted group encompasses only those combinations of substituents and variables that result in a stable or chemically feasible compound. A stable compound or chemically feasible compound is one that, among other factors, has stability sufficient to permit its preparation and detection. In some embodiments, disclosed compounds are sufficiently stable that they are not substantially altered when kept at a temperature of 40° C. or less, in the absence of moisture (e.g., less than about 10%, less than about 5%, less than about 2%, less than about 1%, or less than about 0.5%) or other chemically reactive conditions, for e.g., at least about 3 days, at least about a week, at least about 2 weeks, at least about 4 weeks, or at least about 6 weeks.

As used herein, the terms "combine, combining, to combine, combination" refer to the action of adding at least one chemical substance to another chemical substance(s) either sequentially or simultaneously. In some embodiments, bringing these chemical substances together can result in transformation of the initial chemical substances into one or more different chemical substances. This transformation can occur through one or more chemical reactions, e.g., where covalent bonds are formed, broken, rearranged and the like. A non-limiting example can include hydrolysis of an ester into an alcohol and carboxylic acid which can result from the combination of the ester with a suitable base. In another non-limiting example, an aryl fluoride can be combined with an amine to provide an aryl amine through a substitution process. These terms also include changes in association of charged chemical substances and creation of charged chemical substances, such as, but not limited to, N-oxide formation, acid addition salt formation, basic addition salt formation, and the like. These terms include the creation and/or transformation of radical chemical substances and isotopically labeled chemical substances.

As used herein, the terms "convert", "converting", "to convert" or "conversion" refer to a subset of "combination" and its grammatical equivalents, where the action of one or more reagents transforms one or more functional groups on a chemical substance to other functional group(s). For example, a conversion includes, but is not limited to, transforming a nitro functional group on a chemical substance to an amine with a reducing agent. Conversions also include changes in charged chemical substances, radical chemical substances and isotopically labeled chemical substances. However, the term "convert" does not include alteration of conserved bonds in disclosed genuses and compounds.

Methods of Preparation

In one aspect, the process of the present invention is described in Scheme 5. Acrolein is used as a cheap substitution of chiral glyceraldehyde to conduct Aldol Reaction with fluoropropionate derivatives. The resulting terminal olefin is either halogenized or oxidated and then converted to a gamma lactone directly. The C-4 chiral center of the gamma lactone is inverted by treating with a base and an acid successively to form the desired configuration. With this novel process, the manufacturing can be done efficiently and the cost can be lowered significantly.

Scheme 5

As described in Scheme, the process comprises:
Step a: reacting Acrolein with Fluoropropionate Derivative I to form Aldol Adduct III;
Step b: subjecting to oxidation or halogenation Aldol Adduct III to give Fluorolactone Derivative IV;
Step c: reacting Compound IV with a base followed by treating with an acid medium to produce Compound VI; and
Step d: protecting compound VI with a hydroxyl protecting group to obtain compound VII.

Alodl reaction utilizing Evans N-(α-fluoropropyl)-2-oxazolidinones with TiCl4 is reported in Journal of Fluorine Chemistry 128(2007), 1271-1279. Reactions of N-(α-fluoropropyl)-2-oxazolidinones with aliphatic aldehydes can generate α-fluoropropyl-β-hydroxy-aldol products with high diastereoselectivities. Similar or related reactions can also be found in, for example, Synlett 2004, No. 8, 1371~1374, J. Org. Chem. 2001, 66, 894~902., and J. Am. Chem. Soc. 1997, 119, 7883-7884.

Abbreviations
ACN Acetonitrile
EA Ethyl acetate
DMF Dimethyl formamide
DCM Dichloromethane
DIPEA N,N-Diisopropylethylamine
MTBE Methyl tert-butyl ether
NB S N-Bromosuccinimide
NCS N-Chlorosuccinimide
NIS N-Iodosuccinimide
PE Petroleum ether
THF Tetrahydrofuran Certain specific aspects and embodiments of present invention are described in further detail by the examples below. The illustrated examples are not intended to limit the scope of this invention.

EXAMPLES

Example 1: Preparation of 2-fluoropropanoyl chloride (3)

Chlorosulfonic acid (660 mL, 10 mol, 20 eq) was added to a solution of phthaloyl dichloride (1.4 L, 10 mol, 20 eq) and ethyl-2-fluoropropanoate (600 g, 5 mol) at room temperature. The solution was heated at 120° C. for 4 hs. 2-(R)-fluoropropanoyl chloride was distilled from the reaction mixture under reduced pressure and recovered as a colourless oil (320 g, 58.2%). $^1$H-NMR (CDCl$_3$, 400 MHz): δ 5.08 (dq, J=48.8, 6.8 Hz, 1H), 1.63 (dd, J=22.8, 6.8 Hz, 3H).

Example 2: Preparation of (4R)-3-(2-fluoropropanoyl)-4-isopropyloxazolidin-2-one(4)

n-Butyl lithium (2.5 M in hexane, 30 mL, 75 mmol, 1.1 eq) was added to a solution of 4-(R)-4-isopropyl-2-oxazolidinone (8.8 g, 68.2 mmol, 1 eq) in dry THF (80 mL) at −50° C. under N$_2$ atmosphere. After 30 min, 2-fluoropropanoyl chloride (6.8 mL, 0.9 eq) was added, and the solution was stirred for 4 hs at −50° C. The reaction was then quenched with a saturated solution of NH$_4$Cl (50 mL), extracted with MTBE (80 mL*2), washed with brine and dried over MgSO$_4$. Solvents were removed under reduced pressure. The product was purified over silica (Hexane/EtOAc=10/1) and recovered as a brown oil (9 g, 74.8%). $^1$H-NMR (CDCl$_3$, 400 MHz): δ 6.00 (dm, J=49.2 Hz, 1H), 4.27-4.53 (m, 3H), 2.43 (dm, J=52.6 Hz, 1H), 1.63 (td, J=23.2 Hz, 3H), 0.92 (dq, J=17.8 Hz, 6H).

Example 3: Preparation of (4S)-3-(2-fluoropropanoyl)-4-isopropyloxazolidin-2-one (5)

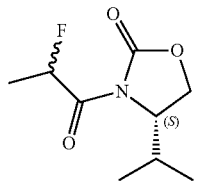

5 n-Butyl lithium (2.5 M in hexane, 75 mL, 187 mmol, 1.1 eq) was added to a solution of 4-(S)-4-isopropyl-2-oxazolidinone (22 g, 170 mmol, 1 eq) in dry THF (200 mL) at −50° C. under N$_2$ atmosphere. After 30 min 2-fuoropropanoyl chloride (17 mL, 153 mmol, 0.9 eq) was added, and the solution was stirred for 1 h at −50° C. After the starting material was completely consumed, the reaction was then quenched with a saturated solution of NH$_4$Cl (125 mL), extracted with MTBE (200 mL*2), washed with brine and dried over MgSO$_4$. Solvents were removed under reduced pressure. The product was purified over silica (hexane/EtOAc=10/1) and recovered as a brown oil (34 g, 83.3%). $^1$H-NMR (CDCl$_3$, 400 MHz): δ 5.93 (dm, J=48.8 Hz, 1H), 4.19-4.17 (m, 3H), 2.35 (dm, J=52.8 Hz, 1H), 1.55 (td, J=23.6 Hz, 3H), 0.85 (dq, J=18 Hz, 6H).

Example 4: Preparation of (4R)-3-(2-fluoropropanoyl)-4-phenyloxazolidin-2-one (6)

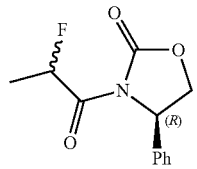

6 n-Butyl lithium (2.5 M in hexane, 13.5 mL, 33.74 mmol, 1.1 eq) was added to a solution of (R)-4-phenyloxazolidin-2-one (5 g, 30.67 mmol, 1 eq) in dry THF (75 mL) at −50° C. under N$_2$ atmosphere. After 30 minutes, 2-fuoropropanoyl chloride (3.75 g, 33.74 mmol) was added, and the solution was stirred for 1 h at −50° C. to −60° C. The reaction was then quenched with a saturated solution of NH$_4$Cl, extracted with EtOAc, washed with NaHCO$_3$(sat), brine and dried over MgSO$_4$. Solvents were removed under reduced pressure. The product was purified over silica (hexane/EtOAc) and recovered as a brown oil (4 g, 55%). $^1$H-NMR (CDCl$_3$, 400 MHz): δ 7.35-7.21 (m, 5H), 5.99-5.84 (md, 1H), 5.42-5.33 (dd, 1H), 4.72 (dd, 1H), 4.31 (m, 1H), 1.50 (m, 3H).

Example 5: Preparation of (4s)-3-(2-fluoropropanoyl)-4-phenyloxazolidin-2-one (7)

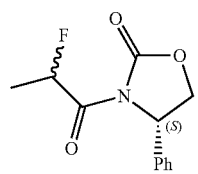

7 n-Butyl lithium (2.5 M in hexane, 67.5 mL, 169 mmol, 1.1 eq) was added to a solution of (s)-4-phenyloxazolidin-2-one (25 g, 153 mmol, 1 eq) in dry THF (375 mL) at −60° C. under N$_2$ atmosphere. After 30 min, 2-fuoropropanoyl chloride (18.7 g, 169 mmol) was added, and the solution was stirred for 1 h at −50° C. to −60° C. The reaction was then quenched with a saturated solution of NH$_4$Cl, extracted with EtOAc, washed with NaHCO$_3$(sat), brine and dried over MgSO$_4$. Solvents were removed under reduced pressure. The product was purified over silica (hexane/EtOAc) and recovered as a brown oil (16.5 g, 45.4%). $^1$H-NMR(CDCl$_3$, 400 MHz): δ 7.36-7.20 (m, 5H), 5.95-5.80 (md, 1H), 5.42-5.30 (dd, 1H), 4.71 (dd, 1H), 4.30 (m, 1H), 1.51 (m, 3H).

Example 6: Preparation of (4S)-4-benzyl-3-(2-fluoropropanoyl)oxazolidin-2-one (8)

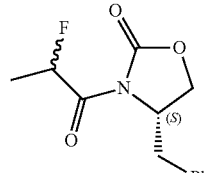

8 n-Butyl lithium (2.5 M in hexane, 54.7 mL, 137 mmol, 1.1 eq) was added to a solution of (S)-4-benzyloxazolidin-2-one (22 g, 124 mmol, 1 eq) in dry THF (220 mL) at −60° C. under N$_2$ atmosphere. After stirring 30 min at −60° C., 2-fuoropropanoyl chloride (15.2 g, 137 mmol) was added dropwisely below −50, after adding the solution was stirred for 1 h at −50° C. to −60° C. The reaction was then quenched with a saturated solution of NH$_4$Cl, extracted with EtOAc, washed with NaHCO$_3$ (sat), brine and dried over MgSO$_4$. Solvents were removed under reduced pressure. The product was purified over silica (hexane/EtOAc) and recovered as a brown oil (25.8 g, 82.7%). $^1$H-NMR (400 MHz, CDCl$_3$): δ 7.29-7.13 (m, 5H), 6.01-5.81 (qd, 1H), 4.71-4.58 (md, 1H), 4.29-4.04 (m, 2H), 3.32-3.16 (dd, 1H), 2.79-2.74 (m, 1H), 1.51 (m, 3H).

Example 7: Preparation of (4R)-4-benzyl-3-(2-fluoropropanoyl)oxazolidin-2-one (9)

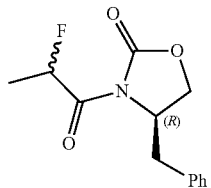

9

Use the procedure described in Example 6, (R)-4-benzyloxazolidin-2-one as the start material to give the desired compound (4R)-4-benzyl-3-(2-fluoropropanoyl)oxazolidin-2-one (yield: 85%). $^1$H-NMR (400 MHz, CDCl$_3$): δ 7.27-7.12 (m, 5H), 6.00-5.83 (qd, 1H), 4.72-4.55 (md, 1H), 4.27-4.03 (m, 2H), 3.32-3.16 (dd, 1H), 2.79-2.72 (m, 1H), 1.53 (m, 3H).

Example 8: Preparation of (4R)-3-(2-fluoropropanoyl)-4-isopropyl-5,5-diphenyloxazolidin-2-one (10)

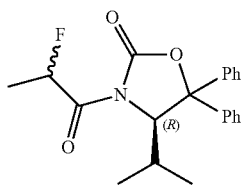

10 n-Butyl lithium (2.5 M in hexane, 48 mL) was added to a solution of (R)-4-isopropyl-5,5-diphenyloxazolidin-2-one (28.1 g) in dry THF (150 mL) at −65° C. under N$_2$ atmosphere. After stirring 30 min at −60° C., 2-fuoropropanoyl chloride (16.4 g, 1.5 eq) was added dropwisely below −60° C. After adding the solution was stirred for 2 h at −60° C. The reaction was then quenched with a saturated solution of NH$_4$Cl, extracted with EtOAc, washed with NaHCO$_3$ (sat), brine and dried over MgSO$_4$. Solvents were removed under reduced pressure. The crude product was recrystallized in (DCM/PE) to give (4R)-3-(2-fluoropropanoyl)-4-isopropyl-5,5-diphenyloxazolidin-2-one (30 g, 85%). $^1$H-NMR (CDCl$_3$, 400 MHz): δ 7.50-7.26 (m, 10H), 5.89 (ddq, J=64.4, 49.3, 6.6 Hz, 1H), 5.37 (dd, J=70.8, 3.4 Hz, 1H), 2.00 (dd, J=7.3, 3.3 Hz, 1H), 1.70 (dd, J=23.4, 6.7 Hz, 1.5H), 1.12 (dd, J=23.8, 6.6 Hz, 1.5H), 0.83 (ddd, J=28.0, 16.7, 6.9 Hz, 6H).

Example 9: Preparation of (4S)-3-(2-fluoropropanoyl)-4-isopropyl-5,5-diphenyloxazolidin-2-one (11)

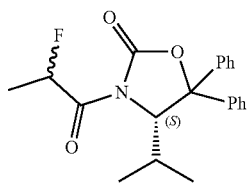

11

Use the procedure described in Example 8 and (S)-4-isopropyl-5,5-diphenyloxazolidin-2-one as the start material to give the desired compound (4S)-3-(2-fluoropropanoyl)-4-isopropyl-5,5-diphenyl oxazolidin-2-one (yield: 82%). $^1$H-NMR(CDCl$_3$, 400 MHz): δ 7.51-7.27 (m, 10H), 5.90 (ddq, J=64.4, 49.3, 6.6 Hz, 1H), 5.38 (dd, J=70.8, 3.4 Hz, 1H), 2.01 (dd, J=7.3, 3.3 Hz, 1H), 1.71 (dd, J=23.4, 6.7 Hz, 1.5H), 1.13 (dd, J=23.8, 6.6 Hz, 1.5H), 0.84 (ddd, J=28.0, 16.7, 6.9 Hz, 6H).

Example 10: Preparation of (R)-3-((2R,3R)-2-fluoro-3-hydroxy-2-methylpent-4-enoyl)-4-isopropyloxazolidin-2-one (12)

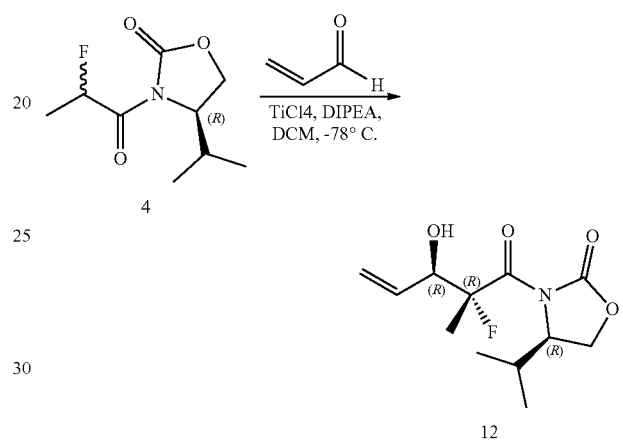

Method A:

TiCl$_4$ (1 M in DCM, 50 mL, 50 mmol, 1.1 eq) was added to a solution of (4R)-3-(2-fluoropropanoyl)-4-isopropyloxazolidin-2-one (4) (10 g, 49.2 mmol, 1 eq) in dry DCM (170 mL) at −78° C. under N$_2$ atmosphere. After 10 min, diisopropylethyl amine (10.3 mL, 1.26 eq) was added and the solution was stirred for 2 hs at −78° C., then the second batch of TiCl$_4$ (1 M in DCM, 50 mL, 50 mmol, 1.1 eq) was added. After 10 min, acrylaldehyde (7 mL, 2 eq) was added and the solution was stirred for 1 h at −78° C. Then the reaction was quenched with a saturated solution of NH$_4$Cl (50 mL). The products were extracted into DCM (20 mL*2), washed with brine and dried over MgSO$_4$. Solvents were removed under reduced pressure and the product was recrystallized in toluene to give the desired compound as a white solid (10.2 g, yield: 80%, purity: 97.2%). $^1$H-NMR (400 MHz, CDCl$_3$): δ 5.89 (dddd, J=17.1, 10.5, 6.5, 0.8 Hz, 1H), 5.42 (d, J=17.2 Hz, 1H), 5.30 (d, J=10.1 Hz, 1H), 4.68 (dd, J=14.8, 6.5 Hz, 1H), 4.44 (d, J=4.0 Hz, 1H), 4.32 (t, J=8.5 Hz, 1H), 4.24 (dd, J=9.1, 3.4 Hz, 1H), 3.61 (d, J=6.5 Hz, 1H), 2.37 (dd, J=7.0, 4.1 Hz, 1H), 1.73 (s, 1.5H), 1.67 (s, 1.5H), 0.92 (ddd, J=7.8, 5.6, 2.4 Hz, 6H); $^{19}$F-NMR (400 MHz, CDCl$_3$): −158.3 ppm.

Method B:

TiCl$_4$ (1 M in DCM, 50 mL, 50 mmol, 1.1 eq) was added to a solution of (4R)-3-(2-fluoropropanoy 1)-4-isopropyloxazolidin-2-one (10 g, 49.2 mmol, 1 eq) in dry DCM (170 mL) at −78° C. under N$_2$ atmosphere. After 10 min, (−)-spartein (14.5 g, 1.26 eq) was added and the solution was stirred for 2 hs at −78° C., then the second batch of TiCl$_4$ (1 M in DCM, 50 mL, 50 mmol, 1.1 eq) was added. After 10 min, acrylaldehyde (7 mL, 2 eq) was added and the solution was stirred for 1 h at −78° C. Then the reaction was quenched with NH₄Cl (sat 50 mL). The products were extracted into DCM (20 mL*2), washed with brine and dried over MgSO₄. Solvents were removed under reduced pressure and the product was recrystallized in toluene to give the desired compound as a white solid (9.4 g, yield: 75%, purity: 96.5%).

Example 11: Preparation of (S)-3-((2R,3R)-2-fluoro-3-hydroxy-2-methylpent-4-enoyl)-4-isopropyloxazolidin-2-one (13)

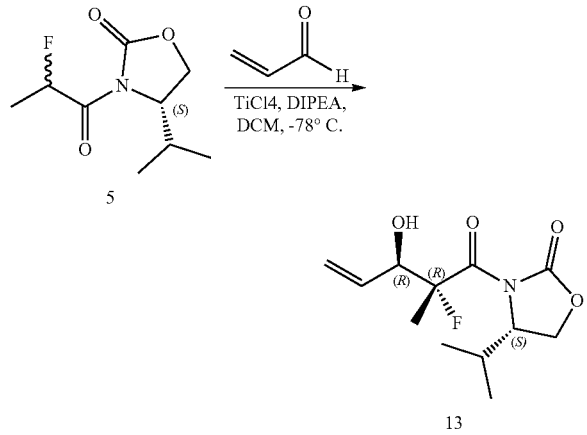

TiCl₄ (1 M in DCM, 50 mL, 50 mmol, 1.1 eq) was added to a solution of (4S)-3-(2-fluoropropanoyl)-4-isopropyloxazolidin-2-one (4) (10 g, 49.2 mmol, 1 eq) in dry DCM (170 mL) at −78° C. under N₂ atmosphere. After 10 min, diisopropylethyl amine (15.9 g, 2.5 eq) was added and the solution was stirred for 2 hs at −78° C. Then acrylaldehyde (7 mL, 2 eq) was added and the solution was stirred for 1 h at −78° C. Then the reaction was quenched with a saturated solution of NH₄Cl (50 mL). The products were extracted into DCM (20 mL*2), washed with brine and dried over MgSO₄. Solvents were removed under reduced pressure and the product was recrystallized in toluene to give the desired compound as a white solid (10.4 g, yield: 83%, purity: 92.8%). ¹H-NMR (400 MHz, CDCl₃): δ 5.92 (d, J=1.1 Hz, 1H), 5.44 (d, J=17.2 Hz, 1H), 5.34-5.28 (m, 1H), 4.73 (dd, J=13.9, 6.2 Hz, 1H), 4.43 (m, 1H), 4.37-4.30 (m, 1H), 4.27-4.21 (m, 1H), 2.43-2.31 (m, 1H), 1.77 (s, 1.5H), 1.71 (s, 1.5H), 0.91 (dd, J=12.1, 7.0 Hz, 6H); ¹⁹F-NMR (400 MHz, CDCl₃): δ −159.1 ppm.

Example 12: Preparation of (S)-4-benzyl-3-((2R,3R)-2-fluoro-3-hydroxy-2-methylpent-4-enoyl)oxazolidin-2-one

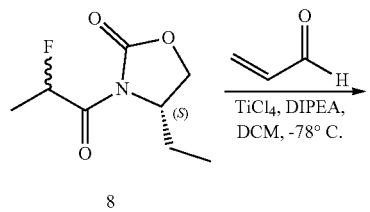

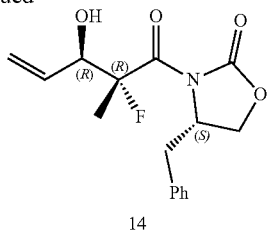

TiCl₄ (1 M in DCM, 50 mL, 50 mmol, 1.1 eq) was added to a solution of (4S)-4-benzyl-3-(2-fluoro propanoyl)oxazolidin-2-one (8) (12.3 g, 49.2 mmol, 1 eq) in dry DCM (170 mL) at −78° C. under N₂ atmosphere. After 10 min, TMEDA (15.9 g, 2.5 eq) was added and the solution was stirred for 2 hs at −78° C. Then acrylaldehyde (7 mL, 2 eq) was added and the solution was stirred for 1 h at −78° C. Then the reaction was quenched with a saturated solution of NH₄Cl (50 mL). The products were extracted into DCM (20 mL*2), washed with brine and dried over MgSO₄. Solvents were removed under reduced pressure and the product was recrystallized in toluene to give the desired compound as a white solid (13 g, yield: 86%, purity: 91.5%). ¹H-NMR (400 MHz, CDCl₃): δ 7.38-7.27 (m, 3H), 7.22 (d, J=6.8 Hz, 2H), 5.96 (dddd, J=17.0, 10.5, 6.2, 1.2 Hz, 1H), 5.47 (d, J=17.2 Hz, 1H), 5.35 (d, J=10.5 Hz, 1H), 4.75 (dd, J=13.9, 6.2 Hz, 1H), 4.66 (td, J=7.1, 3.6 Hz, 1H), 4.23 (dd, J=16.3, 5.0 Hz, 2H), 3.33 (dd, J=13.3, 3.3 Hz, 1H), 2.76 (dd, J=13.3, 10.0 Hz, 1H), 1.81 (s, 1.5H), 1.76 (s, 1.5H); ¹⁹F-NMR (400 MHz, CDCl₃): δ−158.47 ppm.

Example 13: Preparation of (S)-3-((2R,3R)-2-fluoro-3-hydroxy-2-methylpent-4-enoyl)-4-phenyloxazolidin-2-one

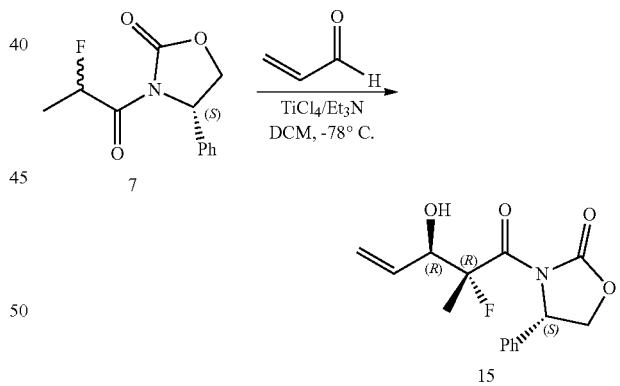

TiCl₄ (1 M in DCM, 50 mL, 50 mmol, 1.1 eq) was added to a solution of (4S)-3-(2-fluoropropanoyl)-4-phenyloxazolidin-2-one(7) (11.6 g, 49.2 mmol, 1 eq) in dry DCM (170 mL) at −78° C. under N₂ atmosphere. After 10 min, Et₃N (12.5 g, 2.5 eq) was added and the solution was stirred for 2 hs at −78° C. Then acrylaldehyde (7 mL, 2 eq) was added and the solution was stirred for 1 h at −78° C. Then the reaction was quenched with a saturated solution of NH₄Cl (50 mL). The products were extracted into DCM (20 mL*2), washed with brine and dried over MgSO₄. Solvents were removed under reduced pressure and the product was recrystallized in toluene to give the desired compound as a white solid (12 g, yield: 83%, purity: 90.5%). ¹H-NMR (400 MHz, CDCl₃): δ 7.43-7.30 (m, 5H), 5.81 (dddd, J=17.0, 10.5, 6.3, 1.1 Hz, 1H), 5.46 (dd, J=8.4, 5.1 Hz, 1H), 5.37 (dt, J=17.2, 1.2 Hz, 1H), 5.23 (d, J=10.4 Hz, 1H), 4.74 (t, J=8.7 Hz, 1H), 4.64 (dd, J=13.5, 6.3 Hz, 1H), 4.31 (dd, J=8.9, 5.2 Hz, 1H), 1.60 (s, 1.5H), 1.55 (s, 1.5H); ¹⁹F-NMR (400 MHz, CDCl₃): δ −158.47 ppm.

Example 14: Preparation of (R)-3-((2R,3R)-2-fluoro-3-hydroxy-2-methylpent-4-enoyl)-4-phenyloxazolidin-2-one

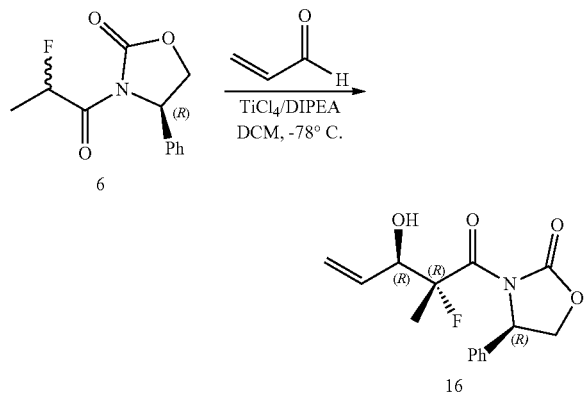

TiCl₄ (1 M in DCM, 50 mL, 50 mmol, 1.1 eq) was added to a solution of (4R)-3-(2-fluoro propan oyl)-4-phenyloxazolidin-2-one (6) (11.6 g, 49.2 mmol, 1 eq) in dry DCM (170 mL) at −78° C. under N₂ atmosphere. After 10 min, DIPEA (15.9 g, 2.5 eq) was added and the solution was stirred for 2 hs at −78° C. Then acrylaldehyde (7 mL, 2 eq) was added and the solution was stirred for 1 h at −78° C. Then the reaction was quenched with a saturated solution of NH₄Cl (50 mL). The products were extracted into DCM (20 mL*2), washed with brine and dried over MgSO₄. Solvents were removed under reduced pressure and the product was recrystallized in toluene to give the desired compound as a white solid (11.1 g, yield: 77%, purity: 91.5%). ¹H-NMR (400 MHz, CDCl₃): δ 7.44-7.29 (m, 5H), 5.74-5.63 (m, 1H), 5.48 (dd, J=8.4, 5.3 Hz, 1H), 5.35-5.26 (m, 1H), 5.15 (d, J=10.5 Hz, 1H), 4.73 (t, 1H), 4.52 (dd, J=14.8, 6.2 Hz, 1H), 4.28 (dd, J=8.9, 5.3 Hz, 1H), 1.68 (s, 1.5H), 1.63 (s, 1.5H); ¹⁹F-NMR (400 MHz, CDCl₃): δ −161.93 ppm.

Example 15: Preparation of (S)-3-((2R,3R)-2-fluoro-3-hydroxy-2-methylpent-4-enoyl)-4-isopropyl-5,5-diphenyloxazolidin-2-one

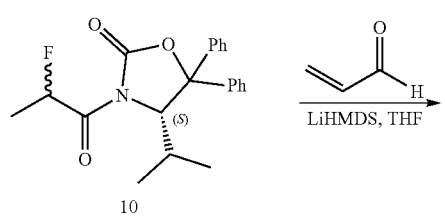

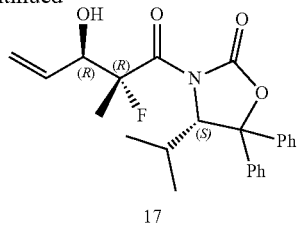

Method 1:

LiHMDS (1 M in THF, 50 mL, 50 mmol, 1.1 eq) was added to a solution of (4S)-3-(2-fluoro propanoyl)-4-isopropyl-5,5-diphenyloxazolidin-2-one(11) (17.4 g, 49.2 mmol, 1 eq) in dry THF (100 mL) at −20° C. under N₂ atmosphere. After 1.5 hs, acrylaldehyde (7 mL, 2 eq) was added and the solution was stirred for 1 h at −20° C. Then the reaction was quenched with a saturated solution of NH₄Cl (50 mL). The products were extracted into EA (50 mL*2), washed with brine and dried over MgSO₄. Solvents were removed under reduced pressure and the crude product was used directly in the next step. m/z (ES+): 412 [M+H]+.

Method 2:

(n-Bu)₂BOTf (1 M in DCM, 50 mL, 50 mmol, 1.1 eq) was added to a solution of (4S)-3-(2-fluoro propanoyl)-4-isopropyl-5,5-diphenyloxazolidin-2-one(11) (17.4 g, 49.2 mmol, 1 eq) in dry DCM (100 mL) at 0° C. under N₂ atmosphere. After 15 min, 2,6-lutidine (10.5 g, 2 eq) was added and the solution was stirred for 2 hs at 0° C. Then acrylaldehyde (7 mL, 2 eq) was added and the solution was stirred for 1 h at 0° C. Then the reaction was quenched with a saturated solution of NH₄Cl (100 mL). The products were extracted into DCM (40 mL*2), washed with brine and dried over MgSO₄. Solvents were removed under reduced pressure and the crude product was used directly in the next step (17.82 g, yield: 88% (Internal standard yield).

Method 3:

(n-Bu)₂BOTf (1 M in DCM, 50 mL, 50 mmol, 1.1 eq) was added to a solution of (4S)-3-(2-fluoro propanoyl)-4-isopropyl-5,5-diphenyloxazolidin-2-one (11) (17.4 g, 49.2 mmol, 1 eq) in dry DCM (100 mL) at 0° C. under N₂ atmosphere. After 15 min, DIPEA (13 g, 2 eq) was added and the solution was stirred for 2 hs at 0° C. Then acrylaldehyde (7 mL, 2 eq) was added and the solution was stirred for 1 h at 0° C. Then the reaction was quenched with a saturated solution of NH₄Cl (100 mL). The products were extracted into EA (50 mL*2), washed with brine and dried over MgSO₄. Solvents were removed under reduced pressure and the crude product was used directly in the next step (16.2 g, yield: 80% (Internal standard yield).

Method 4:

(C₆H₁₂)₂BOTf (1 M in DCM, 50 mL, 50 mmol, 1.1 eq) was added to a solution of (4S)-3-(2-fluoro propanoyl)-4-isopropyl-5,5-diphenyloxazolidin-2-one(11) (17.4 g, 49.2 mmol, 1 eq) in dry DCM (100 mL) at 0° C. under N₂ atmosphere. After 15 min, 2,6-lutidine (10.5 g, 2 eq) was added and the solution was stirred for 2 hs at 0° C. Then acrylaldehyde (7 mL, 2 eq) was added and the solution was stirred for 1 h at 0° C. Then the reaction was quenched with a saturated solution of NH₄Cl (100 mL). The products were extracted into DCM (50 mL*2), washed with brine and dried over MgSO₄. Solvents were removed under reduced pressure and the crude product was used directly in the next step (14.6 g, yield: 80% (Internal standard yield).

Example 16: Preparation of (3R,4R,5R)-3-fluoro-4-hydroxy-5-(hydroxymethyl)-3-methyl dihydrofuran-2(3H)-one Method 1:

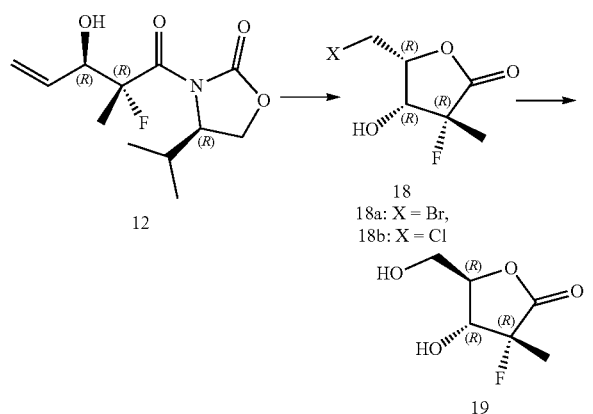

N-Bromosuccinimide (19.6 g, 1.1 eq) was added portion wisely to a solution of (R)-3-((2R,3R)-2-fluoro-3-hydroxy-2-methylpent-4-enoyl)-4-isopropyloxazolidin-2-one(12) (25.9 g, 100 mmol, 1 eq) in DME/H$_2$O (4:1, 130 ml) at −5° C., and stirred for 2 hs. After the reaction was complete, NaHCO$_3$ (sat, 20 mL) was added and stirred for 0.5 h at rt. The mixture were extracted by DCM (50 mL*2), washed with brine and dried over MgSO$_4$. Solvents were removed, the residue dissolved by MTBE (1V), the solid was filtered off to recover the auxiliary, the filtrate was concentrated to dryness to obtained the (3R,4R,5R)-5-(bromomethyl)-3-fluoro-4-hydroxy-3-methyldihydrofuran-2(3H)-one (18a). $^1$H-NMR (400 MHz, CDCl$_3$): δ 4.62-4.53 (m, 1H), 4.37 (dd, J=3.0, 1.9 Hz, 1H), 3.73 (dd, J=10.1, 8.7 Hz, 1H), 3.60 (ddd, J=10.1, 5.8, 1.9 Hz, 1H), 2.59 (dd, J=2.5, 1.7 Hz, 1H), 1.67 (d, J=22.7 Hz, 3H); $^{19}$F-NMR (400 MHz, CDCl$_3$): δ −172.248 ppm.

Alternative Method 1a:

Br$_2$ (17.6 g, 1.1 eq) was added portion wisely to a solution of (R)-3-((2R,3R)-2-fluoro-3-hydroxy-2-methylpent-4-enoyl)-4-isopropyloxazolidin-2-one (12) (25.9 g, 100 mmol, 1 eq) in MeCN/H$_2$O (4:1, 130 mL) between −5° C. to −10° C. and stirred for 2 hs. After the reaction was complete, Na$_2$S$_2$O$_3$ (10%, 20 ml) was added and stirred for 0.5 h at rt then separated. The water phase was re-extracted by DCM (50 mL*2), the combine organic phase was concentrated, dissolved by MTBE (1V), the solid was filtered off to recover the auxiliary, the filtrate was concentrated to dryness to used in the next step.

Alternative Method 1b:

N-chlorosuccinimide (13.3 g, 1.1 eq) was added portion wisely to a solution of (R)-3-((2R,3R)-2-fluoro-3-hydroxy-2-methylpent-4-enoyl)-4-isopropyloxazolidin-2-one(12) (25.9 g, 100 mmol, 1 eq) in 100 ml CH$_3$CN at −5° C., and stirred for 2 hs. After the reaction was complete, NaHCO$_3$ (sat, 20 mL) was added and stirred for 0.5 h at rt. The mixture were extracted by DCM (50 mL*2), washed with brine and dried over MgSO$_4$. Solvents were removed, the residue dissolved by MTBE (1V), the solid was filtered off to recover the auxiliary, the filtrate was concentrated to dryness to obtained the (3R,4R,5R)-5-(chloromethyl)-3-fluoro-4-hydroxy-3-methyldihydrofuran-2(3H)-one (18b), m/z (ES+): 183 [M+H]+.

The related lactone 18a or 18b (0.14 eq) was dissolved in EtOH (104 mL), then KOH (30% in H$_2$O, 50 mL) was added into, the result mixture was reflux for 4 hs. Then HCl (16.7 mL, 12 M) was added into the mixture and reflux for another 2 hs. The solvent was removed and the residue was recrystallized in toluene to give the desired compound as a white solid (yield: 80~85%). m/z (ES+): 165 [M+H]+. $^1$H-NMR (400 MHz, MeOD): δ 4.34 (ddd, J=8.0, 4.2, 2.3 Hz, 1H), 4.02 (ddd, J=17.6, 15.2, 5.1 Hz, 2H), 3.74 (dd, J=13.0, 4.2 Hz, 1H), 1.60 (s, 1.5H), 1.54 (s, 1.5H); $^{19}$F-NMR (400 MHz, MeOD): −172.47 ppm.

Method 2:

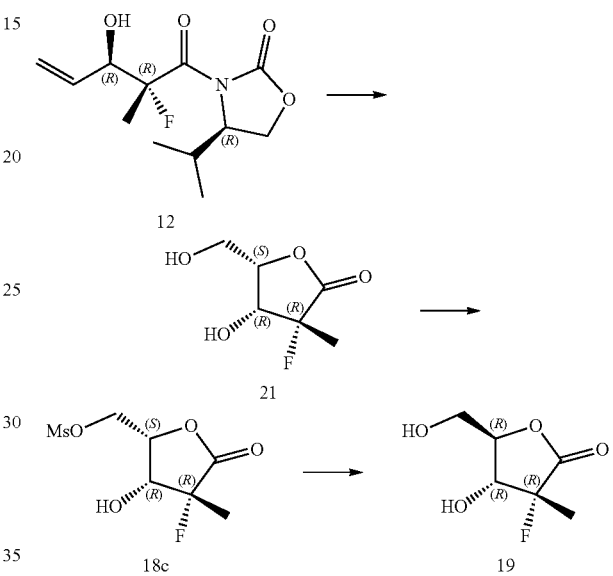

Osmium tetroxide (OsO$_4$) (0.1 equiv) was added in one portion to a stirring solution of the (R)-3-((2R,3R)-2-fluoro-3-hydroxy-2-methylpent-4-enoyl)-4-isopropyloxazolidin-2-one(12) (25.9 g, 100 mmol, 1 eq) in acetone/water (8:1 ratio) under nitrogen. After 5 min, NMO (N-methylmorpholine N-oxide, 60% by weight in water, 1.1 equiv) was added in one portion and stirred for 24 h. The resulting reaction mixture was concentrated under reduced pressure and immediately purified via column chromatography to obtain the desired lactone (3R,4R,5S)-3-fluoro-4-hydroxy-5-(hydroxymethyl)-3-methyldihydrofuran-2(3H)-one (21), yield: 87%, m/z (ES+): 165 [M+H]+.

15.1 g (92.3 mmol) (3R,4R,5S)-3-fluoro-4-hydroxy-5-(hydroxymethyl)-3-methyl dihydrofuran-2(3H)-one (21) was dissolved in 25 mL pyridine and 11.1 g (96.9 mmol) methanesulfonyl chloride was slowly added dropwise at −25 deg C. It was stirred for a day at −25 deg and a day at −10 deg. After adding 20 mL of ethyl acetate and 20 mL water, the solvent was removed on a rotary evaporator. After neutralization with dilute sodium hydrogen carbonate solution, the solvent was removed in vacuo again, the residue was digested with ethyl acetate, the eluate was dried with magnesium sulfate and concentrated in vacuo to dryness. Recrystallization from ethyl acetate/diethyl ether gave a colorless crystalline product ((2S,3R,4R)-4-fluoro-3-hydroxy-4-methyl-5-oxotetrahydrofuran-2-yl)methyl methanesulfonate (18c). Yield: 31%.

33.8 g of ((2S,3R,4R)-4-fluoro-3-hydroxy-4-methyl-5-oxotetrahydrofuran-2-yl)methyl methanesulfonate was dissolved in EtOH (104 mL), then KOH (16.8 g, 3 eq) in H$_2$O (52 mL) was added into, the result mixture was reflux for 4 hs. Then HCl (16.7 mL, 12 M) was added into, the mixture was reflux for another 2 hs. The solvent was removed and the residue was recrystallized in toluene to give the desired compound as a white solid (10.5 g, yield: 45%).

Alternative reagents and reactions to those disclosed above can also be employed. For example, 4-methylbenzene-1-sulfonyl chloride can be used instead of methanesulfonyl chloride. Moreover, primary alcohol can be converted to chloro or bromo by using $Ph_3P/CCl_4$, $PPh_3P/CBr_4$, $PPh_3/NCS$, $PPh_3/NBS$, or $PPh_3/C_2Cl_6$ as a halogenation reagent. The desired product can be obtained in good yields using these reagents and reactions.

Method 3:

Using a method analogous to that described as hereinabove and (S)-3-((2R,3R)-2-fluoro-3-hydroxy-2-methyl pent-4-enoyl)-4-isopropyloxazolidin-2-one(13) as starting material provides the desired compound 19 (yield: 63.2%)

Method 4:

Using a method analogous to that described as hereinabove and (S)-4-benzyl-3-((2R,3R)-2-fluoro-3-hydroxy-2-methylpent-4-enoyl)oxazolidin-2-one(14) as starting material provides the desired compound 19 (yield: 71.8%)

Method 5:

Using a method analogous to that described as hereinabove and (S)-3-((2R,3R)-2-fluoro-3-hydroxy-2-methylpent-4-enoyl)-4-phenyloxazolidin-2-one(15) as the start material gives the desired compound 19 (yield: 65.7%)

Method 6:

Using a method analogous to that described as hereinabove and (R)-3-((2R,3R)-2-fluoro-3-hydroxy-2-methylpent-4-enoyl)-4-phenyloxazolidin-2-oneas(16) starting material provides the desired compound 19 (yield: 59.5%)

Method 7:

Using a method analogous to that described as hereinabove and (S)-3-((2R,3R)-2-fluoro-3-hydroxy-2-methylpent-4-enoyl)-4-isopropyl-5,5-diphenyloxazolidin-2-one (17) as starting material gives the desired compound 19 (yield: 66.7%)

Example 17: Preparation of ((3R,4R)-3-(benzoyloxy)-4-fluoro-4-methyl-5-oxotetra hydro fur an-2-yl)methyl benzoate

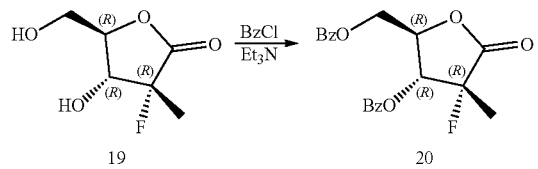

(3R,4R)-3-fluoro-4-hydroxy-5-(hydroxymethyl)-3-methyldihydrofuran-2(3H)-one(19) (25.4 g, 0.154 mol) obtained from example 3 was dissolved in 200 ml of THF. 4-(Dimethylamino)-pyridine (8.2 g, 0.066 mol) and triethylamine (35 g, 0.35 mol) were added and the reaction mixture was cooled to 0° C. Benzoyl chloride (46.0 g, 0.33 mol) was added, and the mixture was warmed to 35-40° C. in the course of 2 hs. Upon completion of the reaction, water (100 mL) was charged and the mixture was stirred for 30 min. Phases were separated and to the aqueous phase methyl-tert-butyl ether (100 mL) was added and the mixture was stirred for 30 min. Phases were separated and the organic phase was washed with saturated NaCl solution (100 mL). The combined organic phases were dried over $Na_2SO_4$ (20 g) filtered and the filtrate was evaporated to dryness. The residue was taken up in iso-propanol (250 mL) and the mixture was warmed to 50° C. and stirred for 60 min, then cooled down to 0° C. and further stirred for 60 min. The solid was filtered and the wet cake was washed with i-propanol (50 mL) and then dried under vacuum. The title compound ((3R,4R)-3-(benzoyloxy)-4-fluoro-4-methyl-5-oxotetrahydrofuran-2-yl)methyl benzoate (47.5 g, 82.6% yield) was obtained. $^1$H-NMR (CDCl$_3$, 400 MHz): 8.10 (d, $J$=7.6 Hz, 2H), 8.00 (d, $J$=7.6 Hz, 2H), 7.66 (t, $J$=7.6 Hz, 1H), 7.59 (t, $J$=7.6 Hz, 1H), 7.50 (m, 2H), 7.43 (m, 2H), 5.53 (dd, $J$=17.6, 5.6 Hz, 1H), 5.02 (m, 1H), 4.77 (dd, $J$=12.8, 3.6 Hz, 1H), 4.62 (dd, $J$=12.8, 5.2 Hz, 1H), 1.77 (d, $J$=23.2 Hz, 3H).

We claim:

1. A compound of formula (IV),

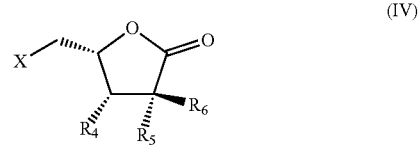

wherein X is a leaving group selected from Cl, Br, I, and a sulfonate of formula R—SO$_3$—; wherein R is methyl, trifluoromethyl, ethyl, phenyl, p-methyl-phenyl, m-methyl-phenyl, o-methyl-phenyl, or naphthalenyl; and wherein R$_4$ is OH, R$_5$ is fluorine, and R$_6$ is methyl.

2. The compound of claim 1, wherein X is Cl, Br, I, mesylate, or tosylate.

3. The compound of claim 1 selected from:

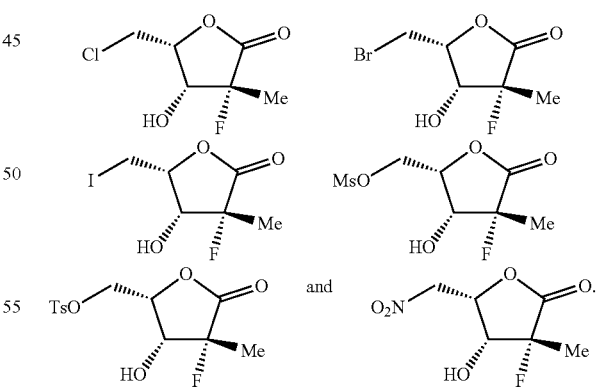

* * * * *